US005998174A

United States Patent [19]
Glorioso et al.

[11] Patent Number: 5,998,174
[45] Date of Patent: Dec. 7, 1999

[54] MULTIGENE VECTORS

[75] Inventors: Joseph C. Glorioso, Cheswick; David Krisky, Pittsburgh, both of Pa.

[73] Assignee: University of Pittsburgh of the Commonwealth System of Higher Education, Pittsburgh, Pa.

[21] Appl. No.: 08/854,601

[22] Filed: May 12, 1997

[51] Int. Cl.⁶ .......................... C12N 15/64; C12N 15/63; C12N 15/38; C12N 15/31

[52] U.S. Cl. .................. 435/91.4; 435/91.41; 435/91.42; 435/91.5; 435/455; 435/463; 435/465; 435/320.1; 536/23.7; 536/23.72

[58] Field of Search .............................. 435/91.4, 172.3, 435/320.1, 91.41, 91.42, 91.5, 455, 463, 465; 536/23.7, 23.72

[56] References Cited

U.S. PATENT DOCUMENTS

| 5,672,344 | 9/1997 | Kelley et al. | 424/93.2 |
|---|---|---|---|
| 5,674,722 | 10/1997 | Mulligan et al. | 435/456 |

FOREIGN PATENT DOCUMENTS

| Wo 95/04139 | 2/1995 | WIPO . |
|---|---|---|
| WO 96/04394 | 2/1996 | WIPO . |
| WO 97/14808 | 4/1997 | WIPO . |

OTHER PUBLICATIONS

Capecchi Altering the genome by homologous recombination Science vol. 244 pp. 1288–1292, 1989.
Geller et al. A defective HSV–1 vector expresses *Escherichi coli* beta–galactosidase in cultured peripheral neurons. Science vol. 241 pp. 1667–1669, 1988.
Glorioso et al., "Gene Transfer to Brain Using Herpes Simplex Virus Vectors", *Annals of Neurology*, 35, 28–34 (1994).
Krisky et al., "Rapid Method for Construction of Recombinant HSV Gene Transfer Vectors", *Gene Therapy*, 4, (10), 1120–1125 (1997).
Leib et al., "Gene Delivery to Neurons: Is Gerpes Simplex Virus the Right Tool the for Job?", *Bioassays*, 15, (8), 547–554 (1993).
Roizman et al., "Genetic Engineering of Novel Genomes of Large DNA Viruses", *Science*, 229, 1208–1214 (1985).
Ace, C.I. et al., *J. Virol.*, 63(5):2260–2269 (1989).
Batterson, W. et al., *J. Virol.*, 46(2):371–377 (1983).
Block, T.M. et al., *J. Virol.*, 64(7):3417–3426 (1990).
Block, T.M. et al., *Virol.*, 192:618–630 (1993).
Bloom, D.C., *J. Virol.*, 68(3):1283–1292 (1994).
Brown, C.R. et al., *J. Virol.*, 69(11):7187–7195 (1995).
Campbell, M.E.M. et al., *J. Mol. Biol.*, 180:1–19 (1984).
Carter, K.L. et al., *J. Virol.*, 70(1):172–178 (1996).
Ciufo, D.M. et al., *J. Virol.*, 68(5):3267–3282 (1994).
Coffin, R.S. et al., *Virol.*, 209:358–365 (1995).
Cook, M.L. et al., *Infect. Immun.*, 7(2):272–288 (1973).
Deatly, A.M. et al., *J. Virol.*, 62(3):749–756 (1988).
DeLuca, N.A. et al., *J. Virol.*, 56(2):558–570 (1985).
Desai et al., *J. Virol.*, 67:6125–6135 (1993).
Deshmane, S.L. et al., *J. Virol.*, 63(2):943–947 (1989).

Deshmane, S.L. et al., *Virol.*, 196:868–872 (1993).
Devi–Rao, G.B., *J. Virol.*, 68(3):1271–1282 (1994).
Dixon, R.A.F. et al., *J. Virol.*, 36(1):189–203 (1980).
Doucas et al., *Genes Devel.*, 10:196–207 (1996).
Dressler et al., *J. Gen. Virol.*, 68:1761–1765 (1987).
Everett, R. et al., *J. Virol.*, 69(11):7339–7344 (1995).
Everett, R.D. et al., *EMBO Journal*, 13(21):5062–5069 (1994).
Everett, R.D. et al., *Virol.*, 180:509–517 (1991).
Everett, R.D., *EMBO Journal*, 3(13):3135–3141 (1984).
Everett, R.D., *Antican. Res.*, 7:589–604 (1987).
Fields, B.N. et al., Eds. *Field Virology* (3rd ed.; Lippincott–Raven Publishers, Philadelphia), 1996, pp. 1795–1847.
Fink, D.J. et al., *Annu. Rev. Neurosci.*, 19:265–287 (1996).
Freeman et al., *Cancer Research*, 53:5274–5283 (1993).
Gaffney et al., *Nucl. Acids Res.*, 13(21):7847–7863 (1985).
Gage, P.J. et al., *J. Virol.*, 66(9):5509–5515 (1992).
Gelman et al., *Proc. Natl. Acad. Sci. USA*, 82:5265–5269 (1985).
Gelman, I.H. et al., *J. Mol. Biol.*, 191:395–409 (1986).
Gelman, I.H. et al., *J. Virol.*, 61(7):2286–2296 (1987).
Glorioso et al., in *Gene Therapeutics: Methods and Applications of Direct Gene Transfer*, Jon A. Wolff, Ed. (Birkhauser Press, Boston, 1994), pp. 281–302.
Hardwicke, M.A. et al., *J. Virol.*, 68(8):4797–4810 (1994)
Hardy, W.R. et al., *J. Virol.*, 68(12):7790–7799 (1994).
Ho, D.Y. et al., *Proc. Natl. Acad. Sci. USA*, 86:7596–7600 (1989).

(List continued on next page.)

*Primary Examiner*—John S. Brusca
*Attorney, Agent, or Firm*—Leydig, Voit & Mayer, Ltd.

[57] ABSTRACT

The present invention provides a method for preparing HSV vectors. The method comprises co-transfecting a source vector and a mutating cassette together into a population of appropriate host cells, such that homologous recombination occurs between the mutating cassette and the source vector whereby the mutating cassette replaces a region of the HSV genome. The mutating cassette has a unique restriction site not present in the sequence of the vector. The method further comprises plaquing the co-transfected host cells, selecting plaques in which recombination has occurred between the source vector and the mutating cassette, and isolating the viral DNA from the plaques. The isolated viral DNA is digested with a restriction endonuclease appropriate for cleaving the viral DNA at the unique restriction site within the mutating cassette to produce two viral polynucleotides. Following purification, the two viral polynucleotides can be ligated to form an HSV vector comprising the two viral polynucleotides. Alternatively, the two isolated viral polynucleotides can be recombined with an insertion cassette to form an HSV vector comprising the insertion cassette at the former locus of the unique restriction site. The present invention further provides a mutant vector, particularly an HSV vector constructed in accordance with the method for the present invention. The present invention further provides a multigene HSV vector, particularly a multigene HSV vector for cancer therapy.

11 Claims, 15 Drawing Sheets

OTHER PUBLICATIONS

Honess, R.W. et al., *J. Virol.*, 14(1):8–19 (1974).
Huang, Q.S. et al., *Gene Therapy* 1:300–306 (1994).
Jang, K. et al., *Nucleic Acids Research*, 19(18):4879–4883.
Javier et al., *Virology*, 166:254–257 (1988).
Johnson, P.A. et al., *J. Virol.*, 68(10):6347–6362 (1994).
Koken, M.H.M., *EMBO Journal*, 13(5):1073–1083 (1994).
Kramer, M.F. et al., *J. Virol.*, 69(3):1389–1399 (1995).
Krisky et al., in *Development of Replication–Defective Herpes Simplex Virus Vectors*, P. Robbins, Ed. (Humana Press, Totowa, NJ).
Kristie, T.M. et al., *Proc. Natl. Acad. Sci. USA*, 83:3218–3222 (1986).
Kristie, T.M. et al., *Proc. Natl. Acad. Sci. USA*, 83:4700–4704 (1986).
Kristie, T.M. et al., *Proc. Natl. Acad. Sci. USA*, 84:71–75 (1987).
Laemmli, U.K., *Nature*, 227:680–685 (1970).
Lium, E.K. et al., *J. Virol.*, 70:3488–3496 (1996).
Marconi, P. et al., *Proc. Natl. Acad. Sci. USA*, 93:11319–11320 (1996).
Maul, G.G. et al., *Journal Gen. Virol.*, 74:2679–2690 (1993).
Maul, G.G. et al., *Journal Gen. Virol.*, 75:1223–1233 (1994).
Maul, G.G. et al., *Virol.*, 217:67–75 (1996).
McCarthy, A.M. et al., *J. Virol.*, 63(1):18–27 (1989).
McGregor, F. et al., *J. Virol.*, 70(3):1931–1940 (1996).
McMahan, L. et al., *J. Virol.*, 64(7):3471–3485 (1990).
Mellerick, D.M. et al.,*Virology*, 158:265–275 (1987).
Meredith, M. et al., *Virol.*, 200:457–469 (1994).
Meredith, M. et al., *Virol.*, 209:174–187 (1995).
Mitchell, W.J. et al., *Journal Gen. Virol.*, 71:125–132 (1990).
Miyanohara, A. et al., *New Biologist* 4:238–46 (1992).
Morris, D.W. et al., *J. Virol.*, 64(4):1794–1802 (1990).
Mullen, M. et al., *J. Virol.*, 69(1):476–491 (1995).
O'Hare, P. et al., *J. Virol.*, 56(3):723–733 (1985).
Post, L.E. et al., *Cell*, 24:555–565 (1981).
Post, L.E. et al., *Cell*, 25:227–232 (1981).
Preston, C.M., *J. Virol.*, 29(1):275–284 (1979).
Puvion–Dutilleul et al, *Exper. Cell Res.*, 218:9–16 (1995).
Ramakrishnan, R. et al., *J. Virol.*, 68(3):1864–1873 (1994).
Ramakrishnan, R. et al., *J. Virol.*, 68;7083–7091 (1994).
Rasty et al., in *Methods in Molecular Genetics*, vol. 7 (Academic Press, 19950 pp. 114–130.
Read, G.S. et al., *J. Virol.*, 46(2):498–512 (1983).
Resnick, J. et al., *J. Virol.*, 63(3):2497–2503 (1989).
Rice, S.A. et al., *J. Virol.*, 68(2):988–1001 (1994).
Rice, S.A. et al., *J. Gen. Virol.*, 69:5550–5559 (1995).
Rixon, F.J. et al., *J. Gen. Virol.*, 71:2931–2939 (1990).
Rock, D.L. et al., *J. Virol.*, 55(3):849–852 (1985).
Rock, D.L. et al., *J. Virol.*, 61(12):3820–3826 (1987).
Roizman, B. et al., in *Field's Virology* (B.N. Fields et al., eds., Raven Press, 1990) pp. 1795–1841.
Roizman, B., in *Perspectives in Virology IV*, (M. Pollard, Ed., Harper & Ros, New York, 1966) pp. 283–304.
Sacks, W.R. et al., *J. Virol.*, 55(30:796–805 (1985).
Sandri–Goldin, R.M. et al., *J. Virol.*, 69(10):6063–6076 (1995).
Sandri–Goldin, R.M. et al.,*J. Virol.*, 70(1):108–118 (1996).
Sauer, B. et al., *Proc. Natl. Acad. Sci. USA*, 84:9108–9112 (1987).
Sawtell, N.M. et al., *J. Virol.*, 66(4):2157–2169 (1992).
Sears, A.E. et al., *J. Virol.*, 55(2):338–346 (1985).
Sedarti, F. et al., *J. Virol.*, 63(10):4455–4458 (1989).
Smith, I.L. et al., *Virol.*, 186:74–86 (1992).
Spivack, J.G. et al.,*J. Virol.*, 61(12):3841–3847 (1987).
Steiner, I., *EMBO Journal*, 8(2):505–511 (1989).
Stevens, J.G. et al.,*Science*, 173:843–845 (1971).
Stevens, J.G. et al., *Science*, 235:1056–1059 (1987).
Stevens, J.G., *Curr. Top. Immunol.*, 70:31–38 (1975).
Sze, P. et al., *Virus Res.*, 26:141–152 (1992).
Uprichard, S.L. et al., *J. Virol.*, 70(3):1969–1980 (1996).
Wang, X. et al., *Circ. Res.*, 78:322–328 (1996).
Ward, P.L. et al., *Trends Genet.* 10:267–274 (1994).
Weis, K. et al., *Cell*, 76:345–356 (1994).
Wu, N. et al., *J. Virol.*, 70(9):6358–6369 (1996).
Wymer, J.P. et al., *J. Virol.*, 63(6):2773–2784 (1989).
Yamada, Y. et al., *J. Infect. Dis.*, 164:1091–1097 (1991).
Yeh, L. et al., *J. Virol.*, 67(12):73773–7382 (1993).

STEP G

HG1

X

STEP H

7H10

X ity of HSV viruses (e.g., ICP47 (including $U_s10-11$),

MULTIGENE VECTORS

STATEMENT AS TO RIGHTS TO INVENTIONS MADE UNDER FEDERALLY SPONSORED RESEARCH AND DEVELOPMENT

This invention was made with Government support under Grant Number DAMD17-94-J-4039 awarded by the United States Army Postdoctoral Training Program in Breast Cancer Biology, and under Grant Numbers RO1-DK49095-01 (JCG), GM-43534-14(JCG), and RO1E411528(DJF) awarded by the United States National Institutes of Health and the Department of Veterans' Affairs. The Government may have certain rights in this invention.

TECHNICAL FIELD OF THE INVENTION

The present invention relates to a method for preparing HSV vectors and to multigene HSV vectors.

BACKGROUND OF THE INVENTION

Gene transfer technology has wide-ranging utility in a number of applications relating to biological research and the treatment of disease. Central to this technology is a vector for introducing expression cassettes into target cells such that the cassettes can be expressed in the target cells. Examples of such vectors include naked DNA vectors (such as plasmids), viral vectors (such as adeno-associated viral vectors) (Berns et al., *Annals of the New York Academy of Sciences*, 772, 95–104 (1995)), adenoviral vectors (Bain et al., *Gene Therapy*, 1, S68 (1994)), herpesvirus vectors (Fink et al., *Ann. Rev. Neurosci.*, 19, 265–87 (1996)), packaged amplicons (Federoff et al., *Proc. Nat. Acad. Sci. USA*, 89, 1636–40 (1992)), pappiloma virus vectors, picornavirus vectors, polyoma virus vectors, retroviral vectors, SV40 viral vectors, vaccinia virus vectors, and other vectors. Once a given type of vector is selected, its genome must be manipulated for use as a background vector, after which it must be engineered to incorporate exogenous polynucleotides.

A particularly attractive vector system employs recombinant herpes simplex virus (HSV) vectors. HSV attacks the human nervous system after a primary infection of the dermal or mucosal tissues. HSV naturally enters axonal portions of sensory ganglia and is transported to the somas of the cells, whereupon the viral DNA is released to the nucleus (Stevens, *Microbiol. Rev.*, 53, 318–32 (1989); Roizman & Sears, in *Field's Virology*, 2d ed. Raven Press, Fields et al., eds. 1795–1841 (1990)). At that point, the wild-type virus either initiates a lytic cycle characterized by viral replication, or enters a latent phase. During the lytic phase, HSV gene expression proceeds through a well-characterized cascade typified by three discrete phases: Immediate Early (α or IE), Early (β or E), and Late (γ or L). Recombinant HSV viruses can be induced to enter latency by inactivating immediate early genes required for replication (e.g., d120, DeLuca et al., *J. Virol.*, 56, 558 (1985)). During the latent phase, the virus persists in an episomal form for the life of its host (Mellerick and Fraser, *Virology*, 158, 265–75, (1987); Rock and Fraser, *J. Virol.*, 55, 849–52, (1985)), neither interfering with neuronal function nor inducing any autoimmune response (Ramakrishnan et al., *J. Virol.*, 68, 1864–70 (1994); Fruh et al., *Nature*, 375, 415 (1995)).

The HSV viral genome is well characterized, as is its life cycle, and the functions of more than 80 native coding polynucleotides are largely defined. HSV coding polynucleotides are generally contiguous linear sequences, thus facilitating genetic engineering of mutant vectors. Furthermore, as roughly half of the viral genes are dispensable for growth in cell culture, the possibility exists of deleting large segments of the HSV genome to accommodate transgenic material (Roizman & Sears, supra; Glorioso et al., in *Viral Vectors*, Academic Press, New York (Kaplitt & Loewy, eds.) 1–23 (1995)). Theoretically, up to 30 KB of the HSV genome can thus be replaced with exogenous material without requiring complementary host cells for propagation of the virus.

As the HSV genome is so well characterized, its genome is readily manipulated for use as a background vector. For example, it is possible to produce vectors deficient for essential loci as long as the missing translation product is otherwise provided, such as via a helper virus or complementary cell line. In fact, of the IE loci (ICP0, ICP4, ICP22, ICP27, and ICP47), only two (ICP4 and ICP27) are required for viral replication. In the absence of these loci, only other immediate early loci are expressed, and the virus is rendered replication-incompetent in non-complementing cell lines. A replication-deficient HSV virus can be induced to exist in host neural tissue in its persistent latent phase without any apparent pathological effect on the host (Ramakrishnan et al., supra), and defective HSV vectors can persist in a similar state in non-neuronal cells as well.

HSV vectors deficient for only one essential IE locus remain highly cytotoxic to infected cells, largely due to expression of the remaining IE gene products (DeLuca et al., *J. Virol.*, 56, 558–70 (1985); Johnson et al., *J. Virol.*, 66, 2952–65 (1992)). However, further research has indicated that mutants deleted for ICP4, ICP22, and ICP27 demonstrate reduced cytotoxicity over singly deficient vectors (see, e.g., Wu et al., *J. Virol.*, 70(9), 6358–69 (1996)). Furthermore, the deletion of other loci reduces the cytotoxicity of HSV viruses (e.g., ICP47 (including $U_s10-11$), UL41, VP16, UL24; see, e.g., Jacobson et al., *J. Virol.*, 63(4), 1839–43 (1989); Johnson, *J. Virol.*, 68(10), 6347–62 (1994)). As such, multideficient HSV vectors represent a desirable choice for gene transfer technology.

Of course, production of multideficient viruses is one step in developing vectors for expression cassette transfer. The second step is engineering a vector containing exogenous expression cassettes. In many applications of gene transfer technology, the expression of multiple transgenes within the target cells is desirable. For example, coordinate expression of multiple cytokine sequences together with a sequence encoding an activator for an antitumor pro-drug is a potentially effective cancer therapy. Preferably, a vector is engineered such that the multiple transgenes are independently controlled (e.g., each is under regulatory control of a separate promoter) to optimize the expression kinetics. Because replication-deficient HSV vectors can transiently or constitutively express exogenous expression cassettes (Fink et al., *Ann Rev. Neurosci*, 19, 265–287 (1996)), HSV vectors containing multiple exogenous cassettes represent powerful agents for gene transfer applications.

Although attractive choices for gene transfer technology, HSV vectors have not been widely utilized for these therapies as of yet, primarily due to the difficulty in engineering vectors using standard procedures. The standard method for engineering mutant HSV viruses is to cotransfect host cells with the source virus and a polynucleotide comprising the desired mutation flanked by regions homologous to the target site within the HSV genome. Within the host cell, homologous recombination produces desired mutant HSV viruses less than 5% of the time, with the efficiency generally proportionate to the size of the flanking regions. Aside from inherently low efficiency, recombinant viruses often grow at markedly reduced rates vis-à-vis unmodified parental viruses within host cells, and so are easily overgrown. Thus, where the source vector is already deficient for native loci (particularly essential loci) viral growth can be substantially compromised, and the efficiency of recombination reduced accordingly. Therefore, screening plaques for desired recombinants is a laborious process, and the process becomes incrementally more tedious with multideficient HSV vectors, especially so where the desired mutation is not readily selectable.

Methods for increasing the efficiency of recombination have been attempted, but each presents significant drawbacks for quickly developing novel transfer vectors. Site-specific recombinases such as the cre-lox recombination system (reviewed in Kilby et al. *Trends in Genetics*, 9, 413–21 (1993)), have been employed to facilitate introduction of exogenous material into viral genomes (see, e.g., Gage et al., *J. Virol.*, 66, 6509–15 (1992)). By these methods, exogenous polynucleotides are introduced into a recombinase recognition site previously engineered into the HSV genome. Recombinants can be selected by assaying for a reporter construct also present within the cassette. Furthermore, source viruses in which the recombinase recognition site is in a locus conferring growth benefits (e.g., the tk locus) do not enjoy the growth advantages over recombinants as seen in traditional methods. Thus, recombinase-mediated production of vectors is a more efficient method for producing HSV vectors than the co-precipitation method, routinely producing desired recombinants roughly 10% of the time, and in some instances site-specific recombination can be significantly more efficient (Rasty et al., *Meth. Mol. Genet.*, 7, 114–30 (1995)). Despite the gain in efficiency, recombinase-mediated production of vectors presents two significant drawbacks. The first is that the method necessarily incorporates the entirety of any plasmid containing the desired insertion sequence, generally a bacterial plasmid for cloning a desired exogenous cassette. Of course, this requirement partially obviates the advantage inherent in the HSV genome's potentially large capacity to accommodate foreign DNA. Secondly, and more significantly, because the recombinase recognition site is retained (in duplicate) within a recombinant vector, subsequent rounds of site-specific recombination greatly disrupt the vectors and can result in randomization of the genome. Thus, site-specific recombination is not a preferred method for generating HSV vectors comprising multiple transgenes.

In order to enhance the efficiency of vector production, some attempts have been made to introduce unique restriction sites into the HSV genome. For example, in one system, all of the XbaI sites within the HSV genome are removed, and the RSAI site in the unique short region of the genome is changed to an XbaI site (Rixon & McLauchlan, *J. Gen. Virol.*, 71, 2931–39 (1990)). Similarly, another system involves the introduction of a unique PacI site within the LAT region of an HSV mutant lacking 4.1 KB in one LAT copy (i.e., the HFEM mutant) (Huang et al., *Gene Therapy*, 1, 300–06 (1994)). With either of these systems, double-digestion of source vector DNA with the appropriate restriction enzyme permits efficient insertion of cassettes. Furthermore, screening of recombinants is achieved using a selectable marker (i.e., β-galactosidase), which increases overall efficiency. However, these methods are limited to introducing exogenous DNA only at these loci, and generally only permit introduction of single cassettes.

Engineering HSV vectors to include multiple cassettes has proven difficult. Not only are the aforementioned methods inefficient for developing multigene HSV vectors, but certain properties of the HSV genome have thwarted attempts to create multiple insertions using standard means. For example, during replication, the HSV virus reacts to foreign DNA inserted at or near repeat elements. In some cases, a single expression cassette can be effectively introduced, but when the insertion of a second cassette is attempted, the virus reacts by recombining and shuffling its genome, substantially destabilizing the vector. In other instances, insertion of exogenous DNA disrupts viral function as well. Where multiple cassettes contain homologous regions to each other (i.e., a similar promoter, similar polyadenylation sequences, etc.), intragenomic recombination also can occur to destabilize the vector.

In view of the foregoing, there exists a need for a method for efficiently producing multideficient HSV vectors, especially multideficient HSV vectors that can be effectively employed in several successive rounds of mutagenesis. There also exists a need for a method for efficiently inserting exogenous polynucleotides into the HSV genome, and especially a means of creating multigene HSV vectors. There exists a further need for vectors having a multiplicity of transgenes for expression in a host cell (i.e., multigene vectors), and particularly for multigene HSV vectors having independently regulated transgenes.

The present invention provides an efficient method for creating mutant HSV vectors. The present invention further provides a multigene HSV vector having independently regulated transgenes. In particular, the present invention provides an HSV vector for cancer therapy deficient for native HSV polynucleotides and containing multiple pharmacologically active therapeutic transgenes. These and other advantages of the present invention, as well as additional inventive features, will be apparent from the description of the invention provided herein.

BRIEF SUMMARY OF THE INVENTION

The present invention provides a method for preparing HSV vectors. The method comprises co-transfecting a source vector and a mutating cassette together into a population of appropriate host cells, such that homologous recombination occurs between the mutating cassette and the source vector whereby the mutating cassette replaces a region of the HSV genome. The mutating cassette has a unique restriction site not present in the sequence of the vector. The method further comprises plaquing the co-transfected host cells, selecting plaques in which recombination has occurred between the source vector and the mutating cassette, and isolating the viral DNA from the plaques. The isolated viral DNA is digested with a restriction endonuclease appropriate for cleaving the viral DNA at the unique restriction site within the mutating cassette to produce two viral polynucleotides. Following purification, the two viral polynucleotides can be joined to form an HSV vector comprising the two viral polynucleotides. Alternatively, the two isolated viral polynucleotides can be joined with an insertion cassette to form an HSV vector comprising the insertion cassette at the former locus of the unique restriction site. The present invention further provides a mutant vector, particularly an HSV vector constructed in accordance with the method for the present invention. The present invention further provides a multigene HSV vector, particularly a multigene HSV vector for cancer therapy.

The present invention will prove highly useful in biological research. Specifically, the present invention provides reagents and methods enabling biologists to more easily study HSV molecular genetics and cytotoxicity. Additionally, the present invention provides reagents and methods permitting biologists to investigate the cell biology of viral growth and infection. Furthermore, the multigene vectors of the present invention will equip the biologist with novel tools for investigating molecular and cellular biology of gene expression and regulation in novel genetic backgrounds. Such studies, for example, can focus on the interaction between gene products in a defined or selected cellular background, the ability of transcription factors to transregulate gene expression via promoter, repressor, or enhancer elements engineered into the HSV vector, etc.

The present invention also will prove highly useful in the clinical setting. Specifically, the present invention permits the rapid and efficient construction of HSV vectors for gene therapy applications. Furthermore, multigene vectors of the present invention are useful vehicles for introducing batteries of therapeutic transgenes into the cells of patients to treat a host of diseases ranging from neoplasms, autoimmune diseases, neurological diseases (such as neurodegenerative disorders), hormonal imbalances, and the like.

The invention may best be understood with reference to the accompanying drawings and in the following detailed description of the preferred embodiments.

BRIEF DESCRIPTION OF THE DRAWINGS

FIG. 9A depicts examples of the products of mutation cassette insertion. FIG. 9B depicts examples of the products of mutation cassette excision.

DESCRIPTION OF THE PREFERRED EMBODIMENTS

Definitions

Figure 1:
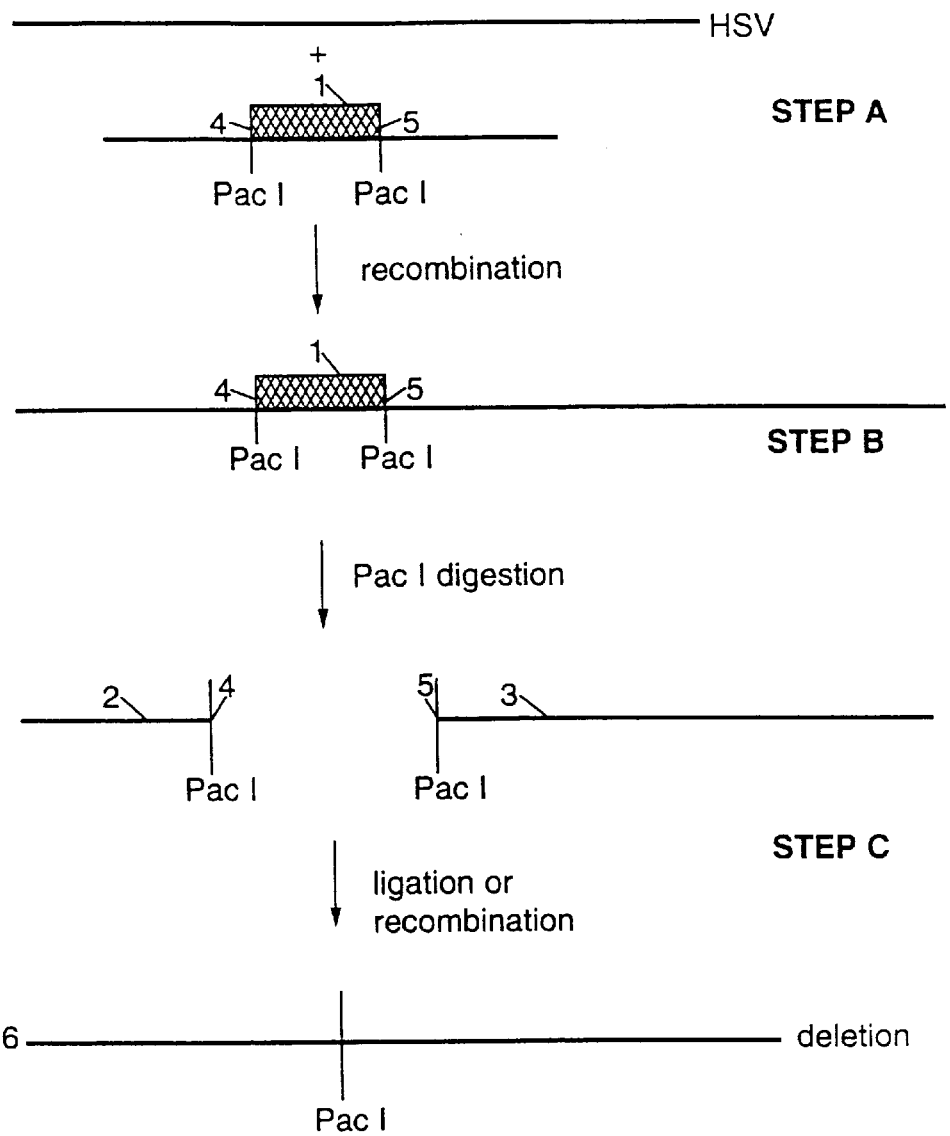
FIG. 1 is a schematic depiction of major steps (A–D) in the present inventive method for mutating HSV viruses.
Figure 1:
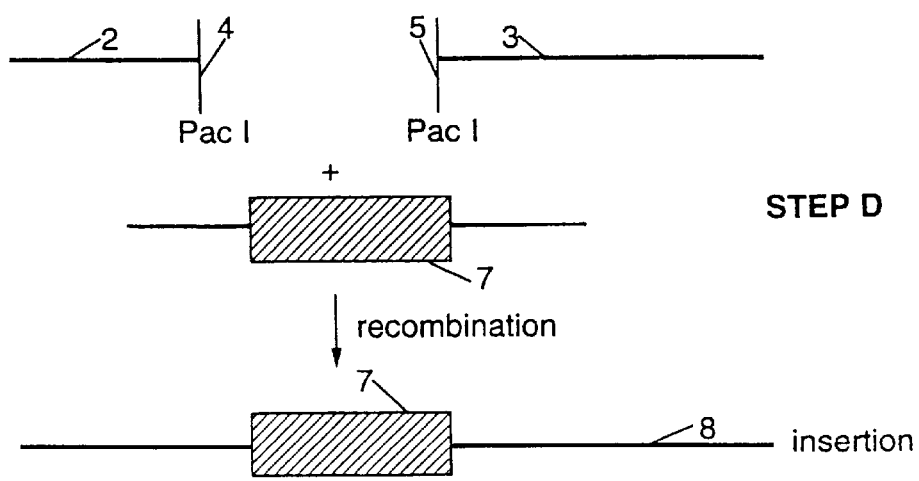

As used herein, including the claims appended hereto, the following terms mean:

A cassette is any polynucleotide sequence having a discrete and identifiable structure. A cassette can comprise a vector or it can comprise a component of a vector. A cassette can include one or more nucleic acid sequences. An example of a cassette is one that contains a promoter element, one or more nucleic acid sequences for expression, and a polyadenylation sequence.

A consensus sequence is a DNA sequence, as well as any degenerate variation of that sequence, to which a DNA binding factor, such as a restriction endonuclease, binds with relative specific affinity. In this context, the scope of degeneracy is governed by the degree to which given nucleotides of a consensus sequence can be deleted, added, or substituted without significantly affecting the relative specificity of binding between the consensus sequence and the DNA-binding factor.

A polynucleotide is expressed if it is transcribed into an RNA transcript.

A polynucleotide is any portion of a nucleic acid molecule which is identified by a specific sequence of nucleotides.

A restriction site is a consensus sequence for a particular restriction endonuclease.

A promoter is a polynucleotide required for transcription at significant levels of a second polynucleotide to which it is operably linked.

A protein is any molecule composed of at least two amino acids wherein each bond between the amino acids is a peptide bond, regardless of whether such molecule includes moieties other than amino acids, such as, for example, saccharides, phosphates, etc. Accordingly, the term "protein" includes polypeptides as well.

A selectable marker is any polynucleotide whose expressed product permits a person to selectively propagate a cell that contains it.

A transgene is a polynucleotide, the expression of which is induced or amplified in a given cellular milieu by introducing into a cell an exogenous nucleic acid, such as a cassette containing the transgene under the control of appropriate promoters and/or transcription factors.

A vector is any polynucleotide competent for introducing one or more exogenous nucleic acid sequences into a cellular environment.

An expression cassette has a polynucleotide for expression operably linked to a promoter. As used herein, when an expression cassette is identified by a particular translation product, the polynucleotide for expression of that cassette encodes the relevant translation product. Thus, for example, a "B7.1 expression cassette" comprises a polynucleotide for expression encoding B7.1 operably linked to a promoter.

HSV includes any HSV-1 or HSV-2 virus or derivative thereof.

IEp refers to any immediate early promoter.

A multigene vector is a vector having a plurality of (i.e., two or more) non-native expression cassettes.

A multideficient vector is a vector having a plurality of (i.e., two or more) mutations in native loci.

Non-native (or not native) refers to any element not present within a given system of reference. Thus, an element not native to HSV is any element not present within a wild-type HSV vector. A non-native element can comprise native sub-elements. Thus, a non-native expression cassette can comprise a native polynucleotide for expression operably linked to a non-native promoter, a non-native polyadenylation sequence, or even a native promoter, if that promoter is not operably linked to the coding polynucleotide in the native state (e.g., the operable linkage is not native).

Operably linked means that separate nucleic acid sequences are functionally associated such that an event at one can precipitate a response from the other. Two or more operably linked nucleic acid sequences can, in combination, comprise an independent genetic element, such as an expression cassette.

Method for Preparing Mutant Vectors

The present invention provides a method for preparing mutant vectors. The method comprises co-transfecting a source vector and a mutating cassette together into a population of appropriate host cells such that homologous recombination occurs between the mutating cassette and the source vector to replace a portion of the gene within the homologous region (FIG. 1, step A). The mutating cassette has a unique restriction site not present in the sequence of the vector. The method further comprises plaquing the co-transfected host cells, selecting plaques in which recombination has occurred between the source vector and the mutating cassette, and isolating the viral DNA from the plaques. The isolated viral DNA is then digested with a restriction endonuclease appropriate for cleaving the viral DNA at the unique restriction site within the mutating cassette to produce two viral polynucleotides (FIG. 1, step B). The method further comprises joining (e.g., by ligation, recombination or other suitable methods) the two viral polynucleotides to form an HSV vector (FIG. 1, step C). Alternatively, the two isolated viral polynucleotides can be joined with an insertion cassette to form an HSV vector comprising the insertion cassette at the former locus of the unique restriction site (FIG. 1, step D).

The mutating cassette has a unique consensus site for a restriction endonuclease not present in the sequence of the source vector. Most preferably, the mutating cassette has two restriction sites not present in the sequence of the vector, such as two identical restriction sites. The two identical sites, thus, flank a region for excision. The region for excision flanked by the two unique restriction sites comprises any length of the cassette. For example, the restriction sites can form the borders of the nonhomologous sequence. Preferably, the region for excision flanks less than the entire nonhomologous sequence, such as, for example, a sequence encoding a selectable marker (FIG. 2, PRC2).

Placement of the paired unique restriction sites thus facilitates excision of the flanked region from the remainder of the viral genome. The skilled artisan will be able to engineer cassettes with such paired unique restriction sites to selectively permit excision of some, but not all, of the cassette from the vector. Thus, for example, the mutating cassette can comprise a promoter operably linked to, and 5' of, a sequence encoding a selectable marker, which is in turn operably linked to, and 5' of, a polyadenylation sequence (see, e.g., FIG. 2). Placement of one restriction site between the promoter and the coding sequence, and the second restriction site between the coding sequence and the polyadenylation sequence, permits the selective excision of the coding sequence from the vector while retaining the promoter and the polyadenylation sequence, thereby facilitating the insertion of another coding polynucleotide.

The 3' and 5' regions of the mutating cassette preferably comprise polynucleotide sequences homologous to the genome of the source vector. Such homologous regions facilitate the introduction of the cassette into the source vector by homologous recombination within a suitable host cell. In this manner, a specific locus of the source vector can be targeted for mutation. Homologous recombination can target any desired loci for mutation.

The mutating cassette also can be an expression cassette, encoding any protein of interest. Preferably, the mutating cassette encodes a selectable marker for facilitating the selection of plaques comprising cells in which recombination has occurred between the source vector and the mutating cassette by screening for the selectable marker. Any known selectable marker is within the scope of the present inventive method, such as galactokinase, β-galactosidase, chloramphenicol acetyltransferase (CAT), β-lactamase, etc. A preferred selectable marker is β-galactosidase, such as the LacZ coding polynucleotide illustrated, for example, in FIG. 2. Applications in which the mutating cassette is an expression cassette, as has been described, are preferred as such applications greatly increase the efficiency of recombination mutagenesis procedures. While the expression of a selectable marker does not, by itself, overcome the inherent inefficiency of homologous recombination (as is described herein), a selectable marker permits rapid identification of even a very few recombinant plaques among many harboring unmodified source vectors.

The first step of the method for the present invention comprises co-transfecting a source vector and a mutating cassette together into a population of host cells. The present inventive method encompasses any suitable viral vector as a source vector (e.g., adenoviri, picornaviri, etc.). Preferably, the source vector is a herpesvirus vector, such as an HSV vector. A source HSV vector can be further deficient in an HSV native locus. Thus, for example, the source vector can be deficient in one or more loci such that the source vector is replication-incompetent, such as, for example, an HSV vector deficient for the products of an essential HSV coding region (e.g., ICP4 or ICP27, see, e.g., DeLuca et al., *J. Virol.*, 56, 558–70 (1985)). In other embodiments, the source vector is replication-competent. Additionally, the source vector can have one or more non-native expression cassettes. Such non-native expression cassettes can be of any type. Preferably, a source vector has an α-tk cassette (i.e., a recombinant expression cassette comprising the HSV-tk coding polynucleotide operably linked to an immediate early promoter). For example, the ICP4 promoter promotes expression of coding polynucleotides to which it is operably linked in a strong, but transient, time course (Weir, *Proc. Nat. Acad. Sci. USA*, 90(19), 9140–44 (1993)). Employing an HSV-ICP4-IEp-tk cassette will thus enhance the safety of working with vectors produced in accordance with the present inventive method, because any unintentional recombinant within a host cell (e.g., with a wild-type HSV) possessing the α-tk allele can be rendered non-virulent (e.g., by exposure to gancyclovir).

While the present method can be employed with any viral system, when used with HSV, restriction sites generally not present in the genome include PmeI and PacI. Preferably, the unique restriction site of the expression cassette is a Pac1 site. Also, preferred HSV genomic targets for mutation according to the present inventive methods include, but are not limited to, the ICP4 locus, the ICP22 locus, the ICP27 locus, the ICP47 locus, the ICP0 locus, the UL41 locus, the tk locus, and the gC locus of the HSV genome. Where the target is the HSV ICP22 locus, the insertion most preferably leaves a portion of the 5' end of the coding region intact, such as, for example, from about 1 to about 300 amino acids (e.g., from about 100 to about 250 amino acids, or even about 200 amino acids), as such a mutation can reduce toxicity.

A suitable host cell is any cell in which the mutating cassette and the source vector can undergo homologous recombination to produce a vector substituting the mutating cassette for the targeted region. However, a preferred host cell is a derivative of a VERO cell. Most preferably, where the cell complements an HSV deficiency, the genome of the cell is engineered not to contain flanking regions such as, for example, N23 cells (which complement ICP27), E5 cells (which complement ICP4), and 7B cells (which complement ICP27 and ICP4). Absence of the flanking regions substantially eliminates recombination events generating a wild-type virus.

Any suitable method can be utilized to introduce polynucleotides into host cells, e.g., calcium phosphate precipitation, electroporation, liposome-mediated transfection, microinjection, polybrene-mediated transfer, protoplast fusion, or other suitable method, and such methods are well-known in the art (Sambrook et al., *Molecular Cloning: A Laboratory Manual,* 2d edition, Cold Spring Harbor Press (1989); see also Watson et al., *Recombinant DNA,* Chapter 12, 2d edition, Scientific American Books (1992)).

Subsequent to cotransfer of the source vector and the mutating cassette into the host cells, the method involves plaquing the co-transfected host cells, selecting plaques in which recombination has occurred between the source vector and the mutating cassette, and isolating the viral DNA from the plaques. Methods for growing host cells to produce plaques are well-known in the art. Selecting plaques representing recombinant HSV vectors is accomplished by any means appropriate to the source vector and mutating cassette. As discussed supra, the mutating cassette preferably is an expression cassette encoding a selectable marker. Thus, recombinant HSV vectors are identified by plaques expressing the selectable marker. Most preferably, the selectable marker is LacZ (FIG. 2), and recombinant HSV vectors comprising the mutating cassette are identified by plaques staining blue in accordance with a standard assay for β-gal expression. Any method for subsequently isolating and purifying the recombinant viral DNA is appropriately employed within the parameters of the present inventive method. Such methods are standard procedures well-known to those skilled in the art.

The isolated recombinant viral DNA is next digested with a restriction endonuclease appropriate for cleaving the viral DNA at the unique restriction site within the mutating cassette (FIG. 1, step B). As depicted in FIG. 1, the digestion produces two viral polynucleotides, 2 and 3, each having a complementary restriction endonuclease half-site end 4 and 5, respectively. As mentioned, preferably the mutating cassette has paired unique restriction sites, such as, for example, in which the present inventive method employs two Pac1 sites to produce recombinant HSV vectors. It will be observed that digesting such a recombinant vector produces the polynucleotide for excision 1 between the two unique restriction sites 4 and 5, as well as the two viral polynucleotides 2 and 3. Following the digestion, the two viral polynucleotides are isolated and substantially purified.

Following substantial purification, the two viral polynucleotides can be joined to form a vector comprising the two viral polynucleotides and the unique restriction site (FIG. 1, step C). The joining can occur by any suitable method, such as by ligating the polynucleotides (blunting the ends first, if desired), by recombination between complementary regions of the polynucleotides, or other suitable means. Moreover, the joining can occur in vivo or in vitro. The ligation and/or recombination reaction can produce several erroneous products (e.g., non-viable polynucleotides produced by juncture between two left-half or two right-half viral polynucleotides, non-viable products lacking one or the other viral polynucleotide, non-viable products in which the excised selectable marker is re-incorporated, etc.). Assaying for correct recombinant vectors, therefore, involves selecting correct plaques. Unlike the first round of the present inventive method (which involves transfecting host cells with viable virus and the mutating cassette), this second round preferably involves transfecting host cells with non-viable polynucleotides. Thus, any plaque represents a recombinant event producing a viable virus and screens for many incorrect ligation and/or recombination events producing non-viable products. Furthermore, in the preferred embodiments in which the mutating cassette has a polynucleotide encoding a selectable marker, the absence of that marker from the plaques of this second round further indicates the absence of incorrect juncture. Thus, for example, where the β-gal assay was employed following the first transfection to select for blue plaques indicative of correct insertion of the mutating cassette, white (i.e., non-staining) plaques indicate potentially correct ligation and/or recombination in the second transfection. Viral DNA isolated from plaques representing potentially correct insertions is subsequently assayed (i.e., by Southern blot analysis, sequencing, PCR, etc.) for the correct insertion product.

In some embodiments, the ligation and/or recombination reaction reconstitutes the unique restriction site from the mutating cassette, thus producing a viral vector comprising the unique restriction site 6 (FIG. 1, step C). As mentioned, in preferred embodiments the mutating cassette has two restriction sites not present in the sequence of the source vector. The result of the ligation and/or recombination reaction, thus, reconstitutes a restriction site from the two half-sites of the viral polynucleotides, producing an HSV vector comprising the unique restriction site and not comprising the region for excision from the mutating cassette. The present inventive method can be repeated through several rounds of insertion, digestion, and ligation and/or recombination to produce multideficient vectors and/or vectors comprising multiple restriction sites otherwise not present within the viral genome.

In many applications, the present inventive method is employed to engineer a vector comprising multiple unique restriction sites in one step. For example, in the first step, multiple mutating cassettes can be employed to recombine into the viral genome. Subsequent digestion and re-joining produce a viral vector comprising deletions in each site targeted for insertion of the mutating cassette. Thus, whether in one step or several steps, the present inventive method can produce a viral vector having any number of identical or differing unique restriction sites. Such a vector permits production of multigene vectors in one subsequent step, thereby greatly increasing the efficiency in producing vectors comprising transgenes.

In addition to producing multideficient viral vectors, the present inventive method also can be employed to produce viral vectors comprising non-native expression cassettes. Preferably, as indicated in FIG. 1, the present inventive method further comprises joining the viral polynucleotides 2–3 and an insertion cassette 7 to form a vector 8 comprising the insertion cassette 7 at the former locus of the unique restriction site 1 (FIG. 1, step D). While joining the polynucleotides can be carried out in any suitable fashion as described herein, the recombination occurs most efficiently within host cells which are first co-transfected with the viral polynucleotides and the insertion cassette. The molecular machinery of the host cells forms the desired vector comprising the two viral polynucleotides and the insertion cassette (FIG. 1, step D). A suitable host cell, therefore, is one in which the insertion cassette and the viral polynucleotides can be joined to produce a vector consisting essentially of the two viral polynucleotides and the insertion cassette. Lastly, the recombinant HSV vectors are plaqued, and the viral DNA is thereafter isolated and purified.

The insertion cassette can comprise any polynucleotide of interest. For example, the insertion cassette can comprise a spacer polynucleotide. In other embodiments, the insertion cassette comprises suitable functional polynucleotides, such as, for example, polynucleotides for modulating the transcription of other polynucleotides (e.g., enhancers, promoters, suppressors) or polynucleotides for expression. In preferred embodiments, the insertion cassette is an expression cassette.

Expression cassettes employed in the present inventive method are of any type appropriate for cells containing the cassette to express the protein of interest. Thus, for example, an expression cassette comprises a polynucleotide operably linked to a promoter.

Any promoter and/or enhancer sequence appropriate for controlling expression of polynucleotides from the vector can be used in constructing an expression cassette according to the present inventive method. Such promoter/enhancer elements are well known in the art. Examples of suitable promoters include prokaryotic promoters and viral promoters (e.g., retroviral ITRs, LTRs, immediate early viral promoters, such as herpesvirus IE promoters (e.g., ICP4-IEp and ICP0-IEp), cytomegalovirus (CMV) IE promoters, and other viral promoters, such as Rous Sarcoma Virus (RSV) promoters, and Murine Leukemia Virus (MLV) promoters). Other suitable promoters are eukaryotic promoters, such as enhancers (e.g., the rabbit β-globin regulatory elements), constitutively active promoters (e.g., the β-actin promoter, etc.), signal specific promoters (e.g., inducible promoters, such as a promoter responsive to RU486, etc.), or tissue-specific promoters (e.g., those active in epidermal tissue, dermal tissue, tissue of the digestive organs (e.g., cells of the esophagus, stomach, intestines, colon, etc., or their related glands), smooth muscles, such as vascular smooth muscles, cardiac muscles, skeletal muscles, lung tissue, hepatocytes, lymphocytes, endothelial cells, sclerocytes, kidney cells, glandular cells (e.g., those in the thymus, ovaries, testicles, pancreas, adrenals, pituitary, etc.), tumor cells, cells in connective tissue, cells in the central nervous system (e.g., neurons, neuralgia, etc.), cells in the peripheral nervous system, or other cells of interest).

In addition to a promoter, an expression cassette for use in the present inventive method comprises a polynucleotide for expression. Preferably, the polynucleotide is a synthetic DNA, cDNA or genomic DNA fragment. Thus, the insertion cassette can encode RNA, such as biologically active antisense RNA or ribozymes, or the insertion cassette can encode biologically active proteins.

For applications in which the vector is employed to treat malignant tumors, preferred proteins are antineoplastic agents. For example, the expression cassettes can encode agents for activating prodrugs, recruiting immunoactive cells, enhancing immune response to the tumor, repressing the capacity of the tumor to destroy or suppress lymphocytes, etc. Thus, the insertion cassette can encode α-tk (such as a recombinant cassette comprising an immediate early promoter operably linked to the HSV tk coding polynucleotide), IL2, B7.1, GM-CSF, or other suitable product. Expression cassettes can comprise other polynucleotides, such as a polyadenylation sequence. Also, expression cassettes can have more than one coding polynucleotide.

For application in HSV vectors, the 5' and/or the 3' end of the insertion cassette preferably has a polynucleotide sequence complementary to the sequence within either viral polynucleotide, thus facilitating homologous pairing, as a sequence homology of about 200 bp on either side of the site of cassette insertion readily promotes recombination in HSV vectors. Of course, a homologous region can comprise a polynucleotide greater than 200 bp of homologous DNA. By facilitating homologous pairing, complementary sequences reduce the incidence of erroneous recombination products. However, where the vector has been subject to previous rounds of mutation according to the present inventive method, homologous pairing can occur anywhere a similar cassette has been inserted, potentially decreasing the probability of correct recombination. Therefore, one of skill in the art can choose to engineer the homologous region to comprise significantly less than 200 bp. How much homology to include depends largely upon the nature of the host vector, the number of recombinant cassettes, and the degree to which the vector and/or cassettes share sequence homology. That decision is well within the ordinary skill of the art.

Preferably, juncture of the two viral polynucleotides and the insertion cassette will not reconstitute the unique restriction site. This is preferred to allow a viral vector created in accordance with the present inventive method to serve as a source vector for subsequent rounds of mutagenesis in accordance with the present inventive method.

The insertion cassette, however, can comprise a second restriction site not present within the viral genome. Such a cassette facilitates further insertion of desired cassettes at the locus by means similar to those described above. It is thus seen that cassettes can be designed to facilitate insertion of desired polynucleotide sequences at regions of interest in a single site within the viral genome as well as targeting additional sites for selective incorporation. Engineering different unique restriction sites into the mutating cassette and the insertion cassette substantially reduces the incidence of erroneous genetic manipulation in subsequent cloning steps.

Multigene HSV Vectors

The present invention further provides a mutant HSV vector. A preferred mutant HSV vector is one constructed in accordance with the method disclosed herein. HSV vectors of the present invention, most preferably, can be propagated in the absence of helper viruses (i.e., a preferred mutant HSV vector according to the present invention is a helper-free vector). Such a vector eliminates the problems attendant to most viral vector or amplicon-based systems which depend upon helper virus for adequate titers of recombinant virus, namely the generation of intolerably high frequencies of wild-type, potentially pathogenic viruses.

A mutant HSV vector in accordance with the present invention can be deficient for a native HSV locus (i.e., a polynucleotide for expression). As it is herein demonstrated that any HSV locus can be targeted for mutation, the present invention provides HSV vectors mutant in any desired locus or loci. Desirably, an HSV vector of the present invention has mutations in more than one loci (i.e., a multi-deficient HSV vector). Most preferably, the HSV vector also has a non-native HSV expression cassette.

Mutant vectors of the present invention can contain any type of mutation; suitable mutations are point mutations, temperature sensitive mutations, insertion mutations, deletion mutations, etc. Desirably, the product of a mutant HSV locus is not produced in biologically-active form, if any product is produced at all. An HSV vector according to the present invention can be deficient in any native HSV locus. Preferred mutant HSV vectors are deficient in the group of loci comprising ICP4, ICP0, tk, ICP22, ICP27, ICP47, or UL41. Removal of ICP22 expression greatly amplifies the activity of promoters not native to HSV. Furthermore, joint inactivation of the ICP4, ICP22, and ICP27 loci substantially reduces vector toxicity and reduces background expression of early and late HSV loci to virtually undetectable levels.

A mutant HSV vector according to the present invention is deficient in any desired HSV loci, and such mutant HSV vector can be a multideficient HSV vector. Of course, an HSV vector of the present invention can be deficient for three or more native HSV loci or four or more native HSV loci, such as an HSV vector deficient for ICP4, ICP22, ICP27, and UL41. The present invention also covers HSV vectors deficient for five or more native HSV loci (e.g., an HSV vector deficient for ICP4, ICP22, ICP27, UL41, and gC) or six or more native HSV loci (e.g., ICP4, ICP22, ICP27, UL41, gC, and the native HSV tk locus). In fact, HSV vectors of the present invention can be deficient in substantially any number of native HSV loci, such as vectors deficient for seven or eight HSV loci, or even substantially more HSV loci.

As mentioned, a preferred HSV vector of the present invention comprises a non-native HSV expression cassette. As the invention provides vectors with deficiencies in multiple loci, so too the vector can comprise multiple (i.e., two or more) exogenous expression cassettes (i.e., a multi-gene HSV vector). Thus, an HSV vector of the present invention can have any number of non-native expression cassettes, such as an HSV vector having three or more non-native independent expression cassettes. Preferably, an HSV vector has four or more, or even five or more non-native independent expression cassettes, and HSV vectors of the present invention can have substantially more non-native independent expression cassettes as well (e.g., six, seven, eight or more non-native independent expression cassettes, etc.). However, the number of exogenous expression cassettes within a vector is not necessarily related to the number of deficiencies in native loci.

A non-native expression cassette can comprise a non-native promoter (i.e., a promoter not present within the wild-type HSV genome) operably linked to either a native or a non-native HSV expression polynucleotide. Similarly, a non-native expression cassette can comprise a native HSV promoter operably linked to a non-HSV coding polynucleotide, or even an HSV coding polynucleotide, if the operable linkage is not itself native to HSV. Thus an appropriate non-native expression cassette is any recombinant expression cassette having a non-native operable linkage between a promoter and a polynucleotide for expression.

A vector of the present invention can comprise any non-native HSV expression cassette. Preferably, the vector of the present invention comprises a combination of non-native cassettes and deficiencies in native loci. The identity of expression cassettes, as well as suitable combinations and permutations of expression cassettes, will depend on the purpose for which the vector is to be used. Examples of some desired promoters and coding polynucleotides are presented elsewhere herein, and it is within the skill of a researcher to select desirable cassettes for expression, alone or in combination, within a host cell.

As mentioned, multigene viruses according to the present invention are useful, in part, for clinical therapy. For example, HSV vectors for use in cancer therapy are preferably not deficient for ICP0 and contain a mutation promoting the stable expression of HSV tk, such as a mutation placing the HSV tk polynucleotide under the control of an immediate early promoter (e.g., HSV ICP4-IEp). Such a vector permits the employment of tk-based therapy. For example, tk can activate the pro-drug gancyclovir to promote increased immune surveillance and to activate the killing of tumor cells expressing tk as well as neighboring cells. Furthermore, a mutation operably linking a strong constitutive promoter to tk is preferable in vectors lacking ICP4, as otherwise tk expression diminishes (see Imbalzano et al., *J. Virol.*, 65, 565–74 (1991)). Presence of the ICP0 product strongly promotes expression from non-native HSV promoters (such as promoters in some types of non-native expression cassettes). More preferably, a vector according to the present invention further has mutations in the ICP47 locus and the UL41 locus as well. Deletion of ICP47 greatly increases immune presentation of infected cells, as the ICP47 translation normally interferes with MHC-I presentation of processed antigen on the tumor cell (see, e.g., York et al., *Cell*, 77, 525–35 (1994)). Inactivation of the UL41 locus prevents the host shut-off mechanism from properly functioning, thus promoting full expression of foreign expression cassettes within the tumor cell.

For treatment of certain types of tumors, a preferred HSV vector will comprise expression cassettes conferring antitumor effects. Thus, for example, the expression cassettes can encode cytokines, enzymes for converting prodrugs (e.g., a constitutively active tk cassette), proteins increasing host immune response, or other such suitable antitumor agents. For example, suitable antitumor expression cassettes include B7.1 and B7.2, which are second-signaling molecules required for antigen presentation and which many tumor cells do not express appreciably. Other preferred antitumor expression cassettes include γ-interferon, which promotes the up-regulation of MCH-I and MCH-II, which are required for antigen presentation at the tumor cell surface. Furthermore, antitumor vectors of the present invention can also comprise expression cassettes encoding cytokines, such as IL-1, IL-2, GM-CSF, etc. These molecules recruit immune T-cells and promote their proliferation and activation. Furthermore, an HSV vector of the present invention can comprise an expression cassette encoding a specific tumor antigen. Such an expression cassette greatly facilitates immune response against tumor cells expressing the cassette. Similarly, other suitable antitumor cassettes can be introduced into the vectors of the present invention.

Antitumor vectors of the present invention can be employed to combat tumors by a variety of means. For example, in some applications, a vector of the present invention is injected directly into a tumor to infect cells within the tumor. The infected cells within the tumor express the non-native expression cassettes to stimulate greater immune response against the tumor, to deliver antineoplastic agents within the tumor, to convert prodrugs into locally-effective toxins, or to effectuate some other desirable response. Additionally or alternatively, the vector of the present invention can be injected directly into a non-tumor region to infect cells in vivo. The infected cells express the non-native expression cassettes to stimulate greater immune response against the tumor (e.g., by expressing tumor-specific antigens), to deliver antineoplastic agents, to convert prodrugs into antineoplastic toxins, or to effectuate some other desirable response. Similarly, excised tumor cells can be infected in vitro and reintroduced into the region of the tumor for prophylactic as well as therapeutic effects. Moreover, isolated dendritic cells can be infected with a virus of the present invention in vitro and reintroduced into the patient or host. The infected dendritic cells express the non-native expression cassettes to stimulate greater immune response against the tumor (e.g., by presenting tumor-specific antigens, by expressing immunostimulatory cytokines, etc.). These therapies can be pursued in conjunction with each other to effectively combat neoplasms within a patient.

A multigene HSV vector of the present invention also can be applied as a vaccine. For example, a multigene HSV vector can comprise expression cassettes encoding immunogenic epitopes. Examples of suitable expression cassettes are cassettes encoding epitopes native to viruses (e.g., coat protein epitopes of other viral epitopes), microbes (e.g., epitopes expressed by bacteria, fungi, yeast, parasites, etc.), or epitopes associated with cancers, neoplasms, cysts, or other aberrant tumors or growths. A multigene HSV vaccine vector is utilized by infecting cells of a patient with the vector to stimulate a primary immune response. The inoculation can be repeated with "booster" injections, and the patient's immuno-responsiveness can be monitored, if desired. Subsequently, an agent comprising the epitopes (e.g., a virus, microbe, tumor cell, or other agent) introduced into the inoculated patient effects a secondary response from the patient to more quickly and effectively combat the agent. When the epitopes are viral or microbial epitopes, the strategy substantially reduces or eliminates the problems attendant with the common practice of inoculation with attenuated viruses or microbes. Furthermore, the vaccine strategy can be employed in conjunction with the above-mentioned strategy of injecting tumor cells in that the secondary response against the tumor epitopes can be accentuated by infecting the tumor cells with a vector to express cytokines, immuno-recruiting agents, immuno-activating agents, and the like.

The following examples further illustrate the present invention but, of course, should not be construed as in any way limiting its scope.

EXAMPLE 1 STARTING MATERIAL

Many procedures, such as Southern blots, PCR, vector construction, including direct cloning techniques (including DNA extraction, isolation, restriction digestion, ligation, etc.), cell culture (including HAT selection and growing cells to produce plaques), transfection of cells (including $CaCl_2$ and $CaPO_4$ transfection protocols), and β-galactosidase assays are techniques routinely performed by one of ordinary skill in the art (see generally Sambrook et al., *Molecular Cloning, A Laboratory Manual*, Cold Spring Harbor Laboratory, Cold Spring Harbor, N.Y. (1989); Graham et al., *Virol.*, 52, 456–67 (1973)).

Host Cells

African green monkey (Vero) cells or derivatives thereof are employed as host cells for homologous recombination and viral growth. Vero cell derivatives include E5 cells (DeLuca et al., *Nucl. Acids. Res.*, 15, 4491–4511 (1987)), which complement HSV ICP4 mutants, N23 cells, which complement for the HSV ICP27 product, and 7B cells, which complement for both ICP4 and ICP27.

N23 cells were constructed by transfecting Vero cells with a plasmid containing the HSV native ICP27 expression cassette and an expression cassette comprising the SV40 early promoter operably linked to a polynucleotide encoding neomycin phosphotransferase. Similarly, 7B cells were constructed by transfecting Vero cells with a plasmid encoding the HSV native ICP4 and ICP27 expression cassettes and an expression cassette comprising the SV40 early promoter operably linked to a polynucleotide encoding neomycin phosphotransferase.

Viruses d120

The d120 virus has been previously described (DeLuca et al., *J. Virol.*, 56, 558–70 (1985)). This virus was used as a source vector for constructing the multideficient HSV vectors described herein.

Briefly, this virus is deficient for both copies of the native HSV ICP4 locus. Thus, the d120 virus can only replicate in cells which complement ICP4 (e.g., E5 cells).

5dl1.2

The 5dl1.2 virus has been previously described (McCarthy et al., *J. Virol.*, 63, 18–27 (1989)). This virus was used as a source vector for constructing the multideficient HSV vectors described herein.

Briefly, this virus is deficient for the native HSV ICP27 locus. Phenotypically, the 5dl1.2 virus can only replicate in cells which complement ICP27 (e.g., N23 cells).

ΔSma-UL41

The ΔSma Virus has been previously described (Read et al., *J. Virol.*, 67, 7149–60 (1993)). This virus is deficient for the native HSV UL41 locus. This vector was used as a source vector for constructing the multideficient HSV vectors described herein.

Ktk-lox

This HSV vector is deficient for tk (i.e., tk⁻) by virtue of the insertion of a lox-recognition site within the polynucleotide encoding tk.

Plasmids pko6

Figure 4:
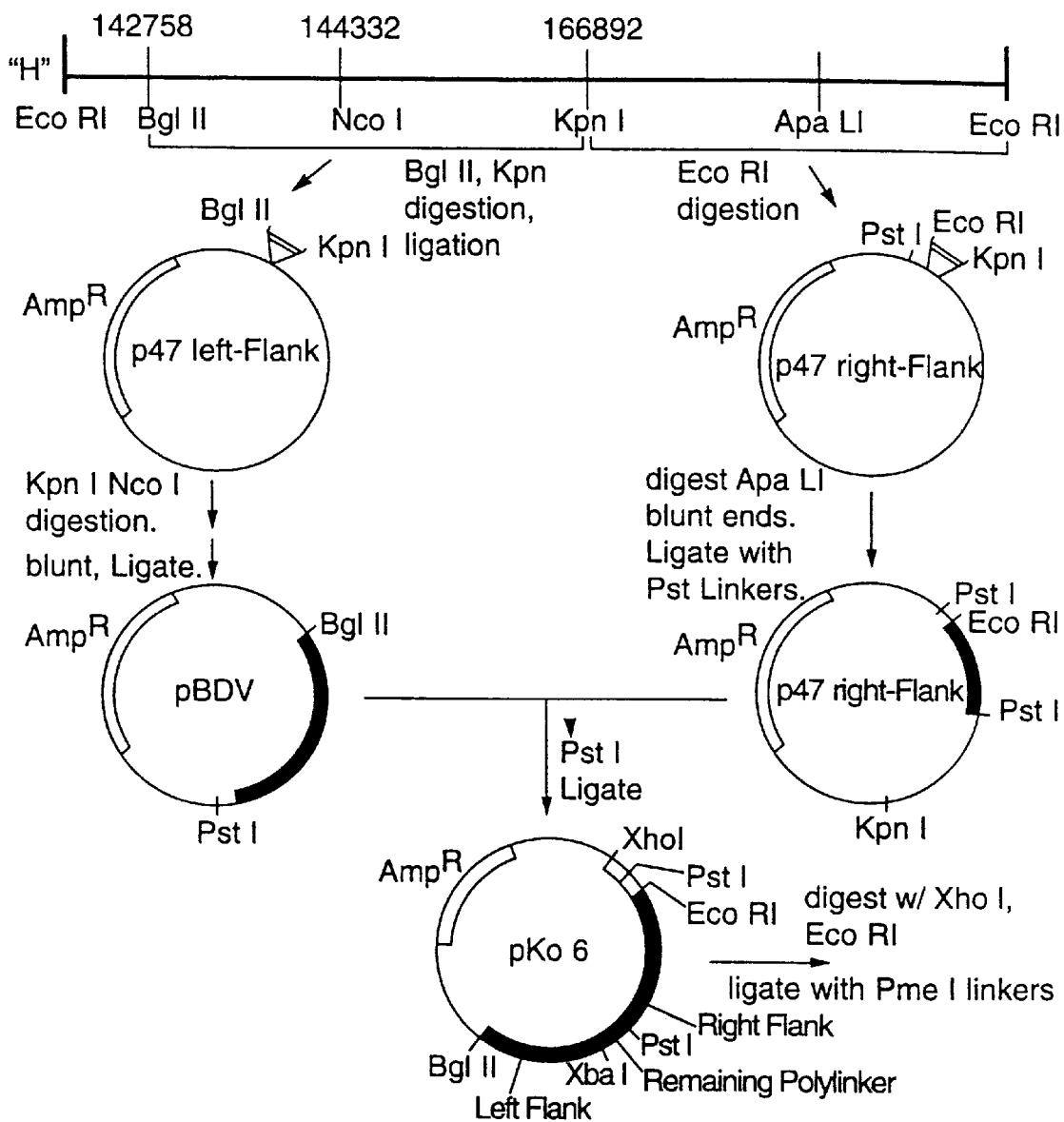
FIG. 4 is a schematic depiction of pko6, a source plasmid for HSV ICP47 homologous DNA, as well as a schematic depiction of a method for constructing pko6.

This plasmid was constructed to introduce a mutation into the ICP47 locus by homologous recombination, and pko6 is depicted in FIG. 4. When recombined into the HSV genome, a roughly 1.1 kb polynucleotide within the ICP47 locus from the ApaLI site (145443) to the NcoI site (144332) is deleted. Furthermore, between these two restriction sites, ko6 is engineered to contain PstI and XbaI sites for insertion of a desired cassette (such as a mutating cassette of the present inventive method).

To construct ko6, the EcoRI-EcoRI "H" fragment was digested with BglII and KpnI to isolate a roughly 2.1 kb polynucleotide (124758–144892), which was ligated into the polylinker of pSP72 (BglII, KpnI). This plasmid was termed 47-left-flank. Subsequently, the 47-left-flank was digested with KpnI and NcoI to remove the fragment spanning from 144332–144892 of the HSV genome, thereby removing the coding sequences for US10 and US11 while leaving the polyadenylation site in tact. The ends were then blunted and the plasmid religated to form pBD2.

Similarly, the EcoRI-EcoRI "H" fragment was digested with EcoRI and KpnI to isolate a roughly 1.8 kb polynucleotide (144892–146693), which was ligated into the polylinker of pSP72 (EcoRI, KpnI). This plasmid was termed 47-right-flank. Subsequently, the 47-right-flank was digested with ApaLI, the ends blunted, and the plasmid relegated with PstI linkers. A PstI digestion, thus, removed the polynucleotide between the EcoR1 and ApaL1 of the ICP47 locus, which was ligated into the pBD2 plasmid (digested with PstI) to form ko6.

Finally, ko6 was digested with XhoI and EcoRI and religated with PmeI linkers to remove the XhoI and EcoRI sites from the plasmid. The resultant plasmid is pko6.

When homologously recombined into the HSV genome, ko6 deletes US10, US11, and ICP47 while leaving the polyadenylation site in tact. Furthermore, the internal XbaI and PstI sites facilitate introduction of a cassette within the region of this deletion.

PRC2

Figure 6:
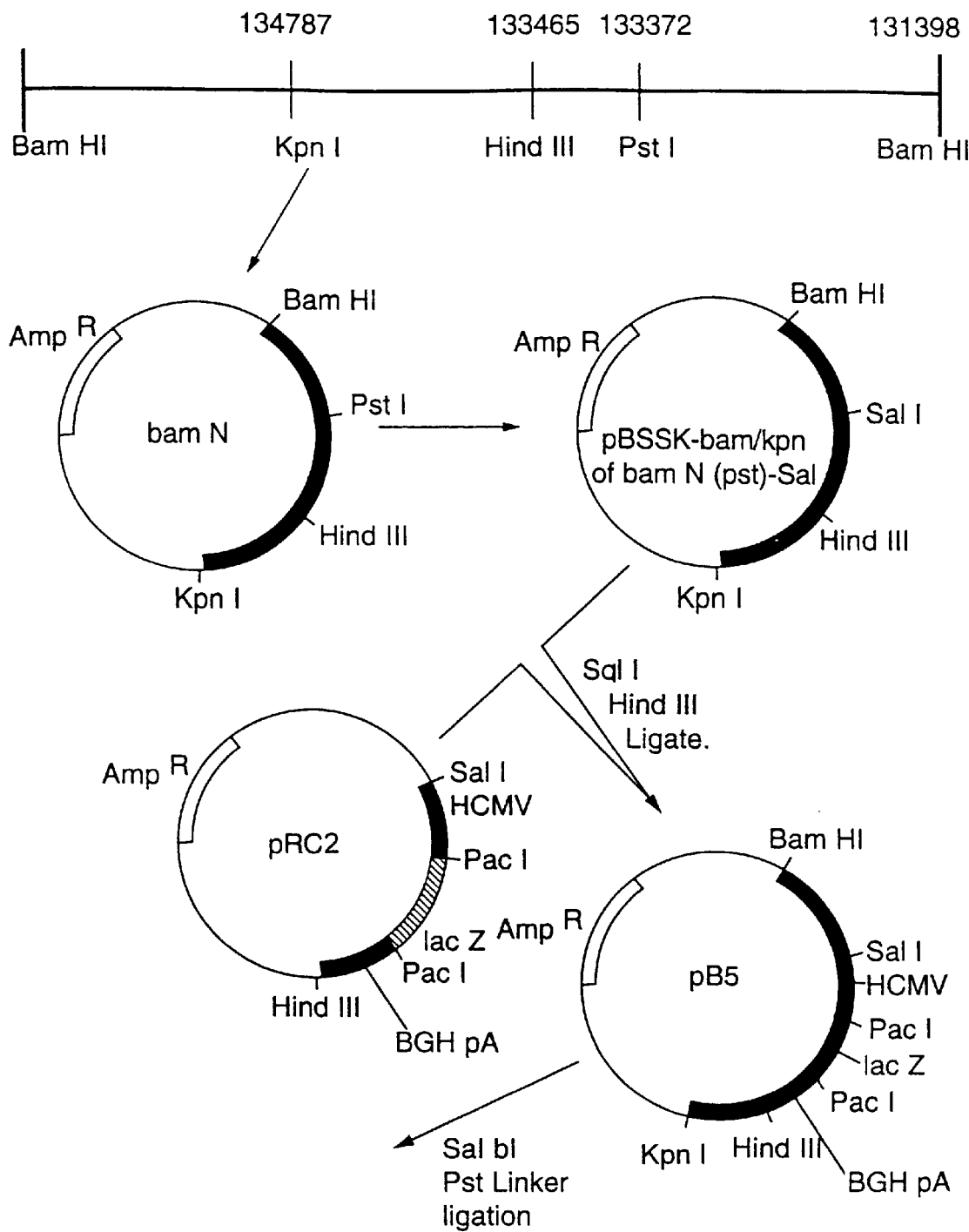
FIG. 6 is a schematic depiction of PB5, a plasmid for introducing a mutating cassette into the HSV ICP22 locus, as well as a schematic depiction of a method for constructing PB5 and a further step for obtaining the mutating cassette from PB5 for insertion into the pko6 plasmid.
Figure 7:
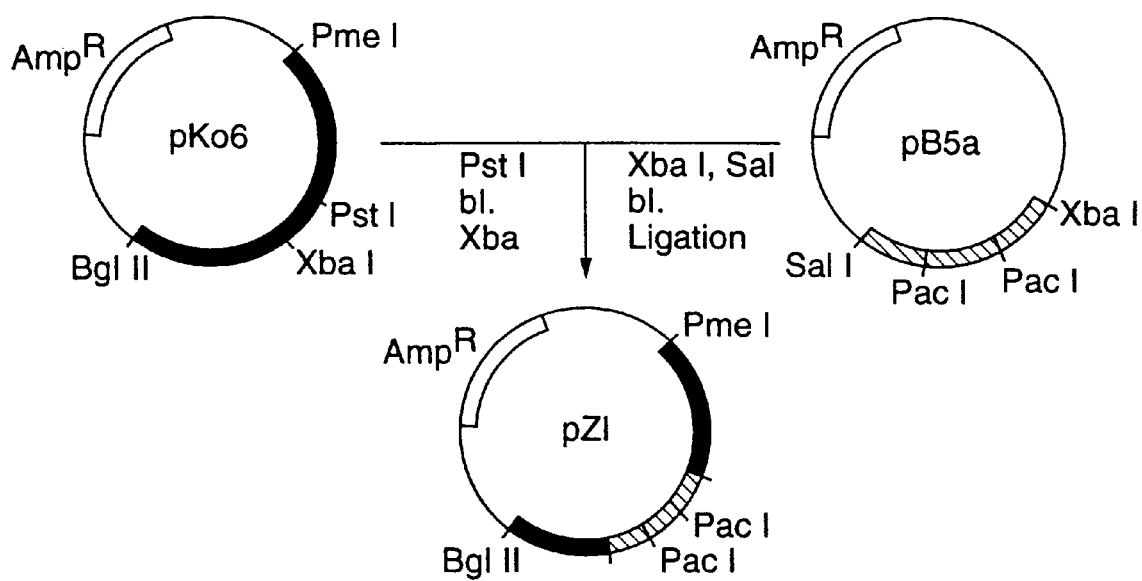
FIG. 7 is a schematic depiction of pZ1, a plasmid for introducing a mutating cassette into the HSV ICP47 locus, as well as a schematic depiction of a method for constructing pZ1 from PB5a and pko6.

This plasmid contains a HCMV-IEp-lacZ-SV40pA mutating cassette for insertion into the HSV native ICP47 or ICP22 locus. The cassette is located within a Xba1-Pst1 fragment on the plasmid and contains two Pac1 sites. Furthermore, PB5 is engineered to introduce a mutation into the ICP22 locus by homologous recombination. The construction of PB5 is indicated in FIG. 6.

Figure 2A:
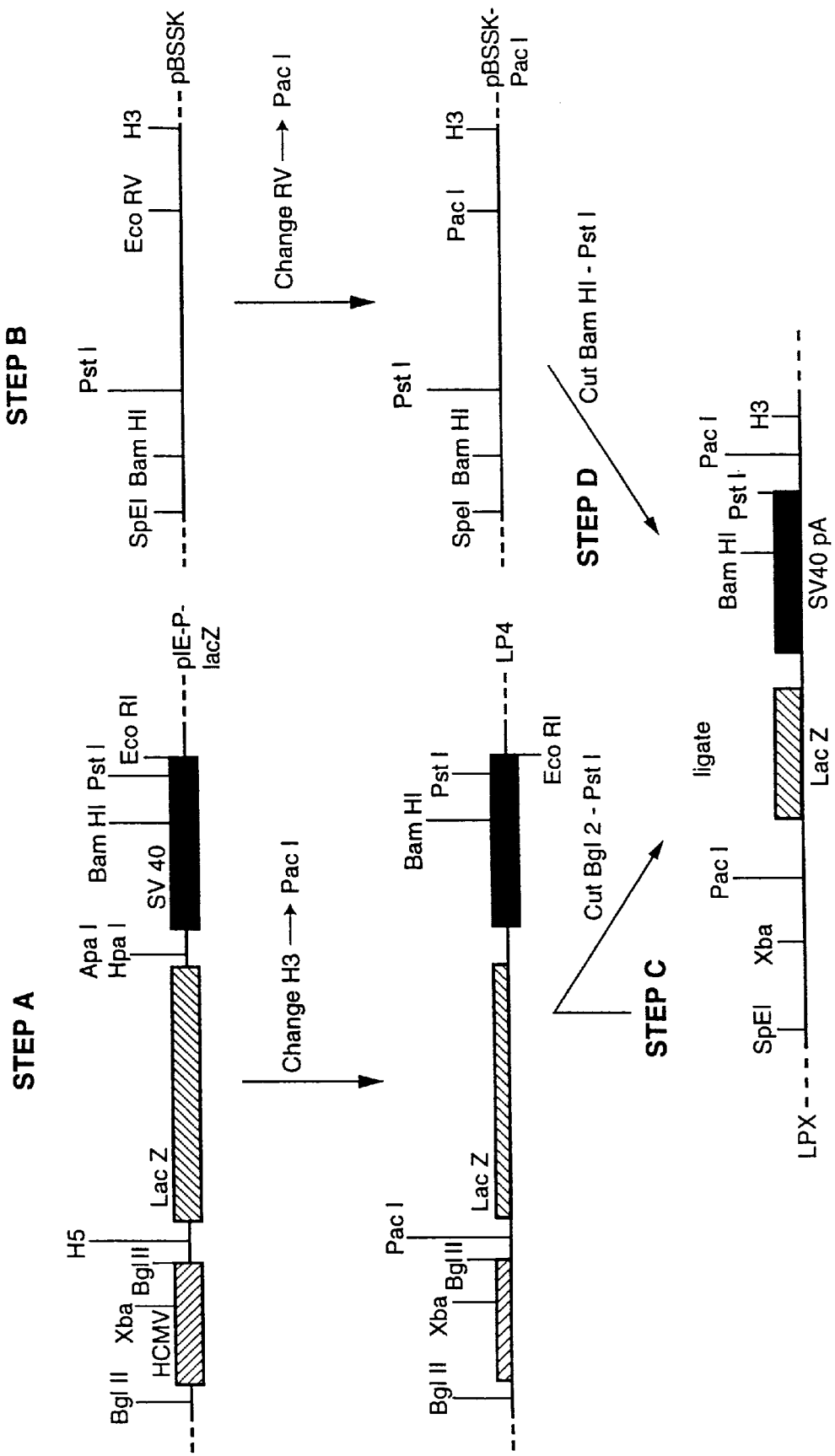
FIGS. 2A–2B schematically depict pRC2, a source plasmid for the HCMV-IEp-lacZ-pA mutating cassette, as well as a method for constructing pRC2.

The Pac1-LacZ cassette was cloned into this plasmid as follows. The PIEP-LacZ source plasmid contains a HCMV-IEp-LacZ cassette within the pBR322 plasmid. A PacI site was introduced into the cassette by mutating the HindIII site by blunting it using the Klenow fragment of DNA polymerase I, and then ligating a PacI linker to the blunt end, followed by religation of the plasmid to create LP4 (FIG. 2A, step A). Similarly, a PacI site was introduced into the EcoRV site within the pBluescript® II SK⁻ plasmid to create pBSSK-PacI (FIG. 2A, Step B).

Following digestion, a BglII-PstI polynucleotide from LP4 was ligated into the BamHI-PstI site of pBSSK-PacI to create the LPX plasmid (FIG. 2A, steps C & D).

Figure 2B:
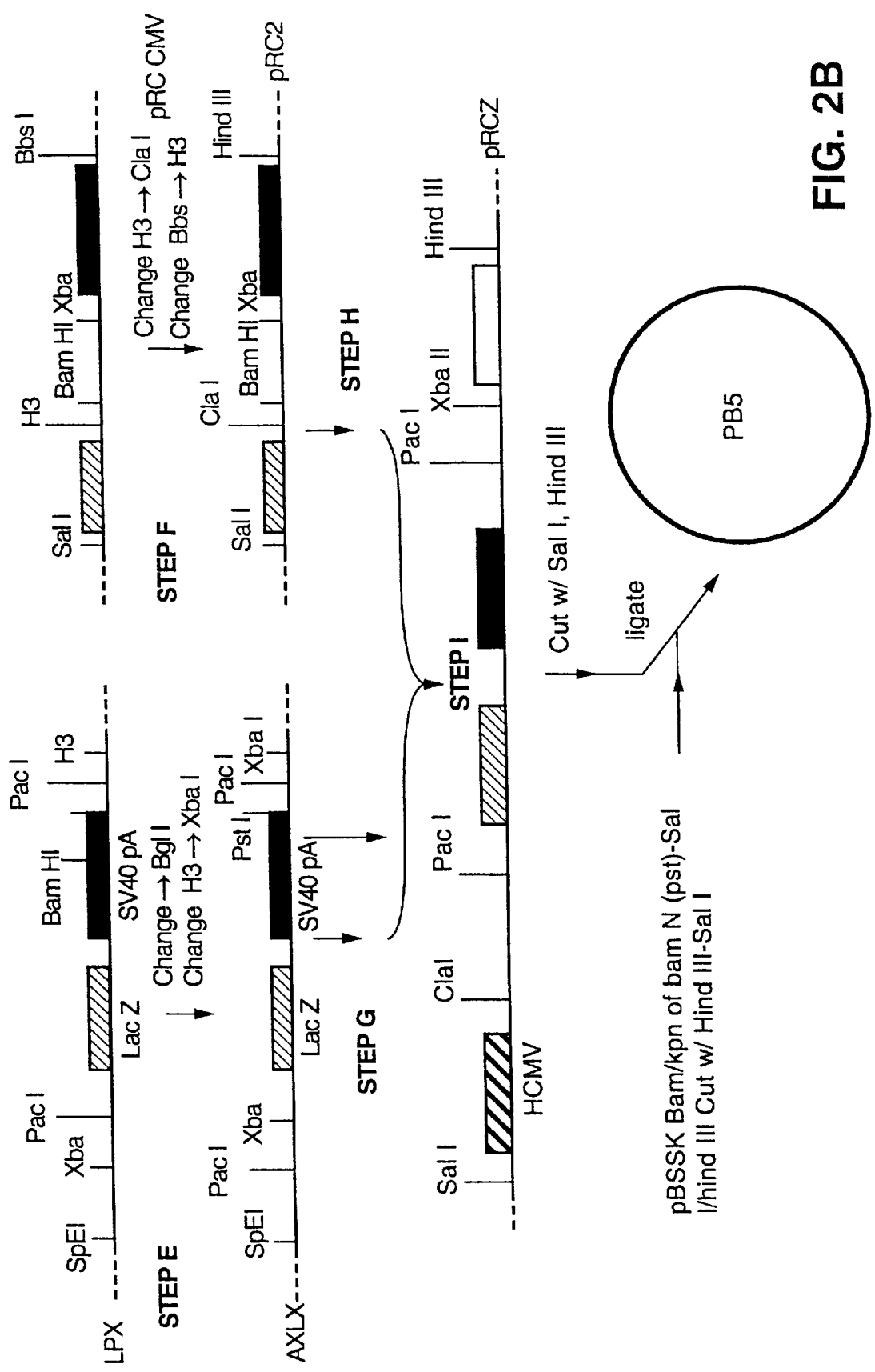

The XbaI sites (both within the cassette 5' of the novel PacI site and within the polylinker pBSSK-II polylinker) were changed to BglII, and the HindIII site was changed to an XbaI site, to create the plasmid AXLX (FIG. 2B, step E). Furthermore, the HindIII site within the pRc-CMV™ vector was replaced with a ClaI site, and the BbsI site following the BGHpA polynucleotide was replaced with a HindIII site, to create pRC2 (FIG. 2B, step F).

Subsequently, the BglII-XbaI polynucleotide comprising the LacZ-Sv40pA sequences from AXLX was ligated into the BamHI-XbaI site of pRC2 to create the PRC2 plasmid (FIG. 2B, steps G–I).

PB5

This plasmid (FIG. 6) facilitates homologous recombination into the ICP22 locus.

The BamHI-BamHI "N" fragment was digested with BamHI and KpnI to isolate a roughly 3.4 kb polynucleotide (131398–134787), which was ligated into the polylinker of pSP72 (BamHI, KpnI) to create the bamN plasmid. Subsequently, this plasmid was digested with PstI (cutting at 133372), the ends blunted, and the plasmid religated with SalI linkers to create pBSSK-bam/kpn of bamN(pst)-salI.

The pBSSK-bam/kpn of bamN(past)-salI plasmid, thus, contains homologous regions to ICP22. Insertion into the ICP22 locus causes a mutation in which the ICP22 protein is truncated at roughly 200 amino acids. By virtue of the Pst1 site, an exogenous polynucleotide can be cloned into pBSSK-bam/kpn of bamN(past)-salI as an HindIII-SalI polynucleotide.

The SalI-HindIII polynucleotide comprising the LacZ-SV40pA sequences from the PRC2 plasmid (FIG. 2) was ligated into the SalI-HindIII site of pBSSK-bam/kpn of bamN(past)-salI to create PB5, following the appropriate restriction digestion.

The LacZ-SV40pA polynucleotide can be removed from PB5 by digesting the plasmid with ClaI and XbaI, which cut outside the double PacI-flanked polynucleotide and between the Sv40pA sequence and the BGHpA sequence (FIG. 2). Thus, an exogenous polynucleotide can be inserted as a ClaI-XbaI polynucleotide, operably linked to both the HCMV-IEp and the remaining BGHpA.

For insertion into the ICP47 locus, the PstI site in the SV40pA of PB5 is destroyed, and the SalI site in the polylinker changed to a PstI site for excision as a PstI-XbaI fragment (pB5A, FIG. 6). Thus, the mutating cassette within PB5 can be cloned into the XbaI-PstI sites of ko6.

UL41 Mutation (p48.2)

Figure 5:
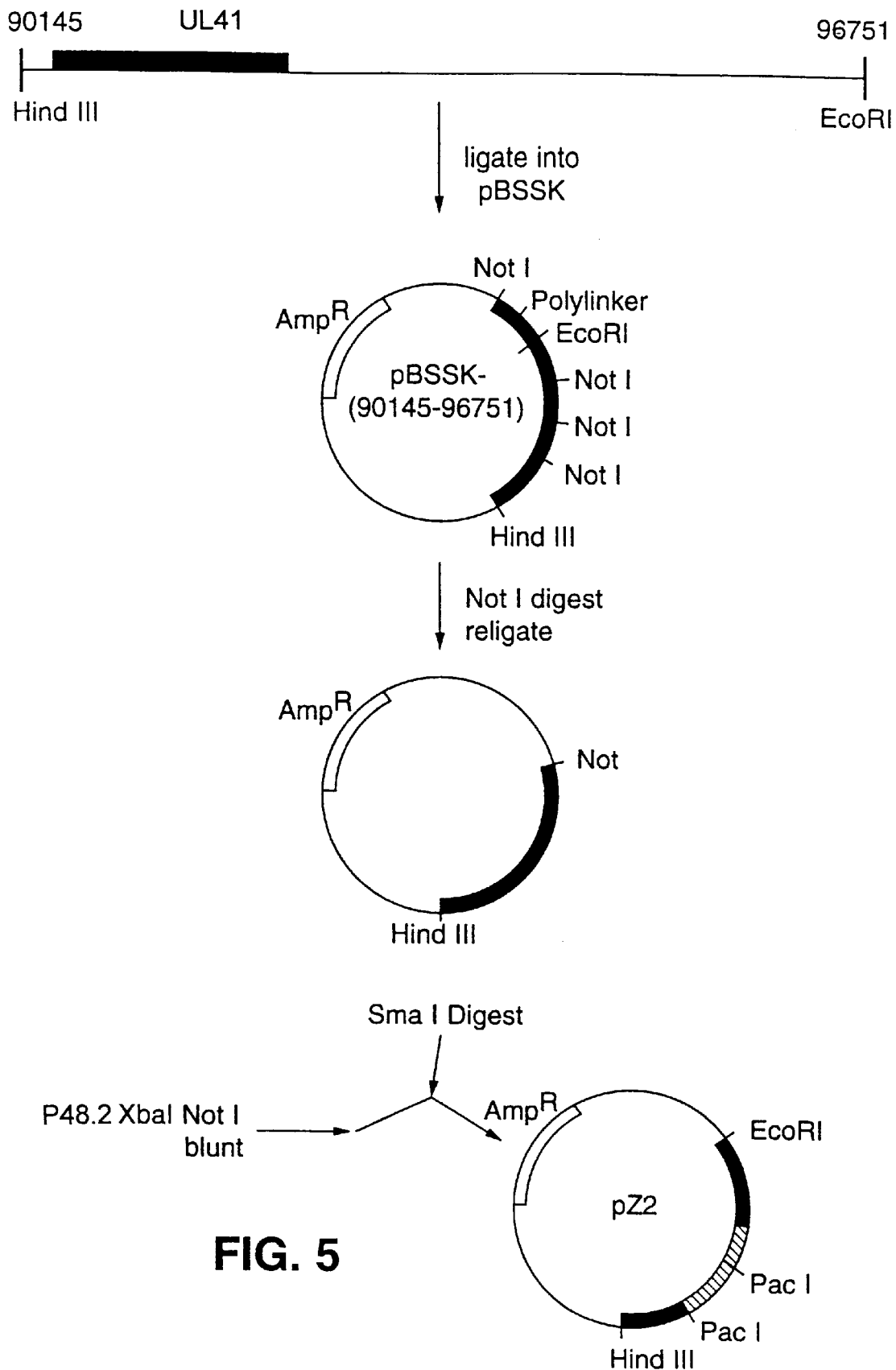
FIG. 5 is a schematic depiction of pZ2, a plasmid for introducing a mutating cassette into the HSV UL41 locus, as well as a schematic depiction of a method for constructing pZ2.

As indicated in FIG. 5, a 6.6 kb EcoRI-HindIII polynucleotide comprising the entire UL41 locus was cloned into the polylinker of pBSSK. The plasmid was thereafter digested with NotI (which cuts at several sites within the region) to retain a 3.7 kb NotI-HindIII polynucleotide (90145–93858 of the HSV genome) within the plasmid. Subsequently, this plasmid was digested with SmaI (which cuts twice within the NotI-HindIII polynucleotide) to excise a 583 SmaI-SmaI polynucleotide representing portions of exon 3 of the UL41 coding region.

Figure 3:
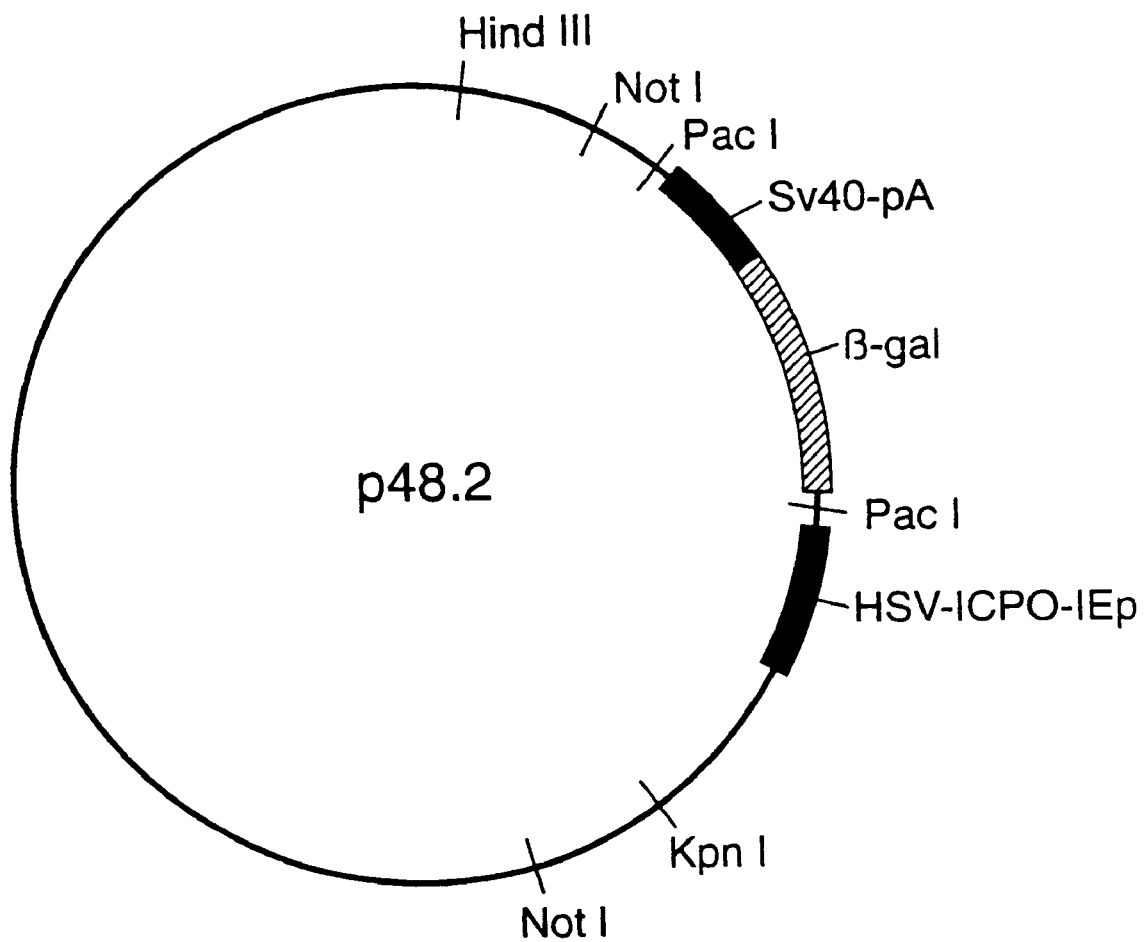
FIG. 3 is a schematic representation of p48.2, a source plasmid for an HSV-ICP0-IEp-lacZ-pA mutating cassette.

A plasmid (p48.2) (FIG. 3) was created to contain the ICP0-IEp-LacZ-SV40pA mutating cassette for insertion into the HSV UL41 locus. A polynucleotide comprising the HSV-1 ICP0-SV40IEp was cloned into the EcoRV site of the plasmid such that it was operably linked to the β-gal construct. The cassette is located within a Xho1-Not1 polynucleotide on the plasmid and contains two Pac1 sites flanking the cassette.

p48.2 was digested with Xho1-Not1 to isolate the polynucleotide comprising the mutating cassette. This polynucleotide was then blunted and cloned into the SmaI linearized plasmid to create pZ2 (FIG. 5) PZ2 facilitates homologous recombination of the HSV-ICP0-LacZ-SV40pA expression cassette into the ICP22 locus.

gC Insertion

The pGC/HCMVg5-GAL4:VP16 vector (Oligino et al., Gene Therapy, 3, 892–99 (1996)) was digested to replace the GAL4:VP16 cassette with a mutating cassette comprising two PacI sites flanking the lacZ coding polynucleotide to create the pGC-lac plasmid. This plasmid, thus, creates a cassette in which the lacZ coding polynucleotide is under the regulation of the HCMV-IEp and is flanked by sequence homologous to the HSV gC locus.

Source of Cassettes for Cre-Lox Recombination into the tk Locus

Figure 8:
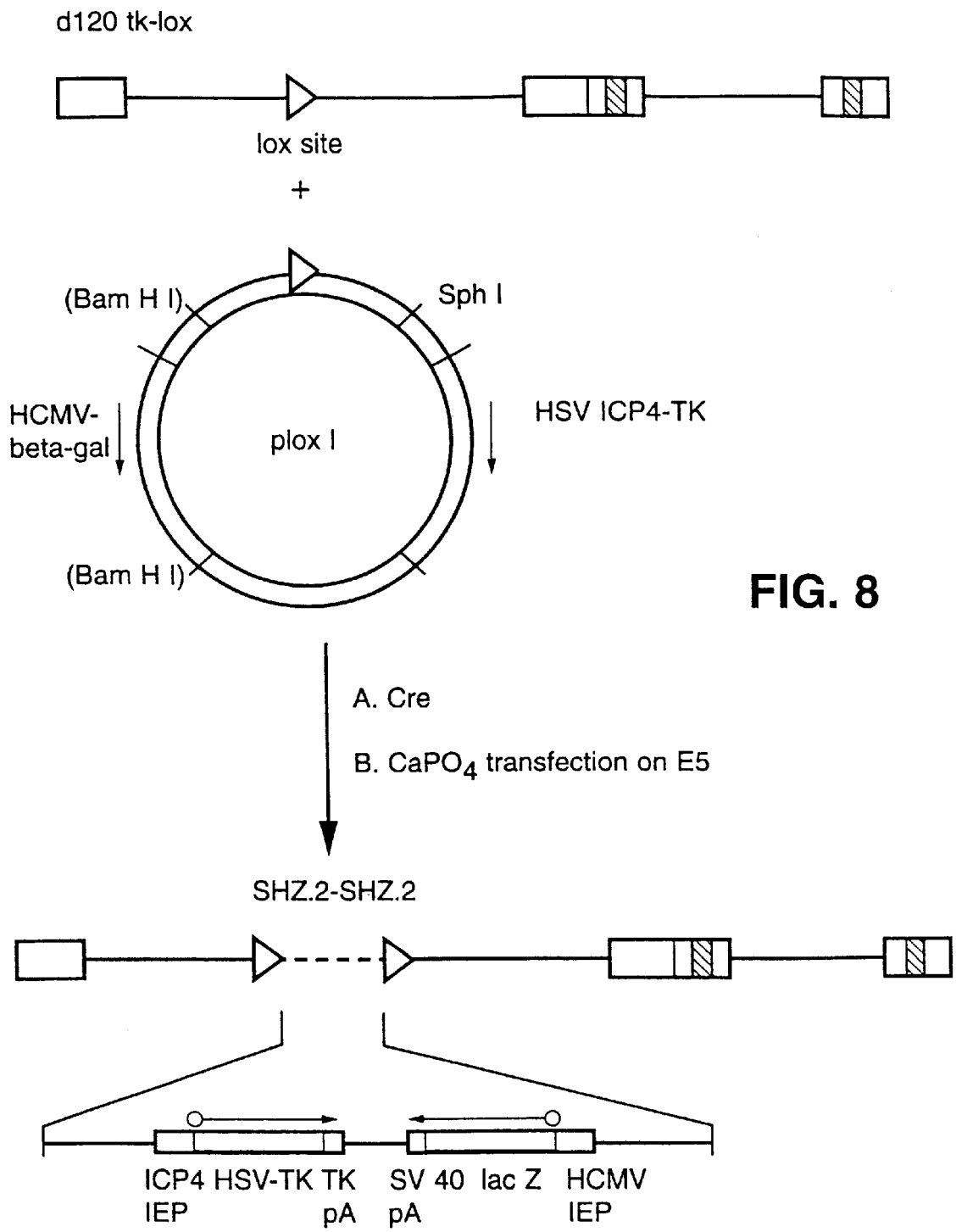
FIG. 8 is a schematic representation of plox-1, a source cassette for cre-lox recombination.

A plasmid (pLox-I) (FIG. 8) was constructed comprising two expression cassettes and a lox site for site-specific recombination. This plasmid has a BamHI-BstEII fragment comprising an HSV expression cassette in which the HSV tk coding polynucleotide is operably linked to the HSV-ICP4 IEp. The plasmid also has a BamHI-BamHI polynucleotide comprising an expression cassette into which the HCMV-IEp is operably linked to a β-galactosidase coding polynucleotide. The lox site is placed between the two cassettes.

A second plasmid (pLox-II) similar to plox-I was also created, but which lacks the HCMV-IEp-β-gal cassette.

Source of ICP4-IEp-tk (α-tk)

A cassette comprising the HSV ICP4-IEp operably linked to the coding region for the HSV-tk coding polynucleotide was created by ligating the "BamP" BamH1-BamH1 fragment spanning the UL22–24 loci of HSV1 into the BamH1 cite of pUC-19 to create the pUCX1 plasmid. The plasmid was then digested with BglII and PstI to excise a fragment representing the native HSV tk promoter and a portion of the UL24 locus. A BglII-HindIII polynucleotide comprising the HSV ICP4-IEp was ligated to the BglII end of the linearized plasmid such that the promoter was operably linked to the tk coding polynucleotide. Subsequently, the plasmid was reconstructed to create an HSV ICP4-IEp-tk cassette within the BamH1-BamH1 polynucleotide.

Source of HCMV-IEp-hIL-2

A cDNA encoding human IL-2 (ATCC 39673 Genetics Institute) was ligated to the 3' untranslated region of the rabbit β-globin gene and the SV40pA sequence, further ligated to place the HCMV-IEp and β-globin intron 5' of the IL-2 coding sequence, and cloned into the pko6 to replace the HCMV-lacZ cassette in pko6.

Source of HCMV-IEp-hB7.1

A cDNA encoding human B7.1 was cloned into the pB5 plasmid such that the coding nucleotide was placed under the control of the HCMV-IE promoter.

Source of ICP0-IEp-hGM-CSF

A cDNA encoding human hGM-CSF (ATCC 57594) was end-modified to form an EcoR1-XbaI fragment and ligated into p41 to replace the lacZ coding sequence and place the coding sequence under control of the HSV ICP0 promoter.

EXAMPLE 2 CREATION OF FIRST ROUND MUTANTS

In order to investigate the efficacy of the present inventive method to create singly and multiply-deficient HSV viruses, a number of mutant viruses were created. Details regarding the construction of each vector are presented in the following subsections.

Each of the viruses was assayed for grown characteristics on 7B cells, E5 cells, N23 cells, and Vero cells, and the genotypes were analyzed through Southern blotting for native tk, ICP22, UL24, UL41, and ICP47. Furthermore, the titer of each stock was measured. These data are presented in Table 1.

precipitated into E5 cells and assayed for blue plaques by the β-gal assay and for the presence of tk expression. Blue plaques were isolated, and the correct insertion was confirmed by Southern blot hybridization.

Growth characteristics and genotype are presented in Table 1.

S4TK

This vector is ICP4$^-$, and contains an ICP4-IEp-tk expression cassette at the UL24 locus. S4tk is depicted schematically in FIG. 10A, step A.

Figure 10A:
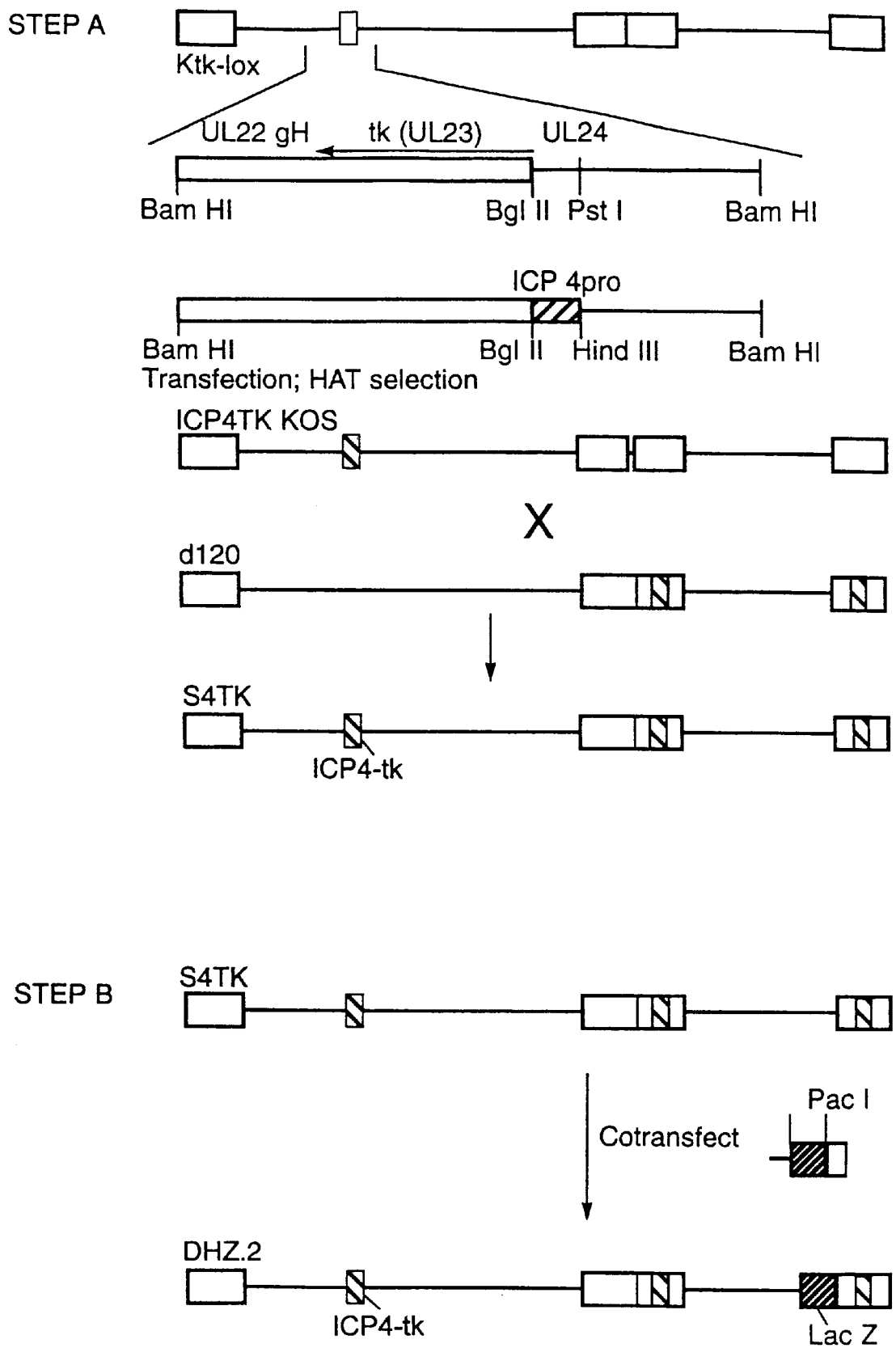
FIGS. 10A–10D schematically depict a method for creating multigene HSV vectors comprising non-native HSV expression cassettes in accordance with the present inventive method.

This vector was created in two steps (FIG. 10A, step A). First, the BamH1-BamH1 polynucleotide comprising the HSV-ICP4-IEp-tk cassette from ploxI was introduced into the HSV genome by homologous recombination into the tk locus of the Ktk-lox vector. Desired recombinants would rescue the tk$^+$ phenotype by eliminating the lox recognition sequence present in Ktk-lox and by placing the tk coding polynucleotide under the control of the constitutive HSV ICP4-IEp; furthermore, the desired recombinants would lack UL24 by virtue of the placement of the exogenous ICP4 promoter within the UL24 coding polynucleotide. Thus, recombinants were selected by the HAT assay in tk$^-$ cells. A desired recombinant virus was selected, and the correct insertion confirmed by Southern hybridization.

TABLE 1

Genotype and Titer for Deficient HSV Vectors

| Vector | Growth Characteristics | | | | Non-Essential Genes Status | | | | | $(10^6)/10^8$ cells |
|---|---|---|---|---|---|---|---|---|---|---|
| | 7B | E5 | N23 | Vero | TK | ICP22 | UL24 | UL41 | ICP47 | |
| SHZ.1 | + | + | − | − | − | + | + | + | + | NT |
| SHZ.2 | + | + | − | − | * | + | + | + | + | 20000 |
| SOZ.1 | + | + | − | − | + | + | − | − | + | 2500 |
| S4TK | + | + | − | − | * | + | − | + | + | 2777 |
| DHZ.1 | + | + | − | − | * | − | − | + | + | 180 |
| DHZ.2 | + | + | − | − | * | + | − | + | − | 1782 |
| DHZ.3 | + | − | + | − | + | − | + | + | + | 210 |
| THZ.1 | + | − | − | − | * | − | − | + | + | 114 |
| THZ.3 | + | − | − | − | * | − | − | − | + | 408 |
| TOZ.1 | + | − | − | − | * | − | − | − | + | 371 |
| D.1 | + | + | − | − | * | − | − | + | + | ND |
| D.2 | + | + | − | − | * | + | − | + | − | ND |
| T.1 | + | − | − | − | * | − | − | + | + | ND |
| T.3 | + | − | − | − | * | − | − | − | + | ND |

ND = No Data

SHZ.1

Figure 9A:
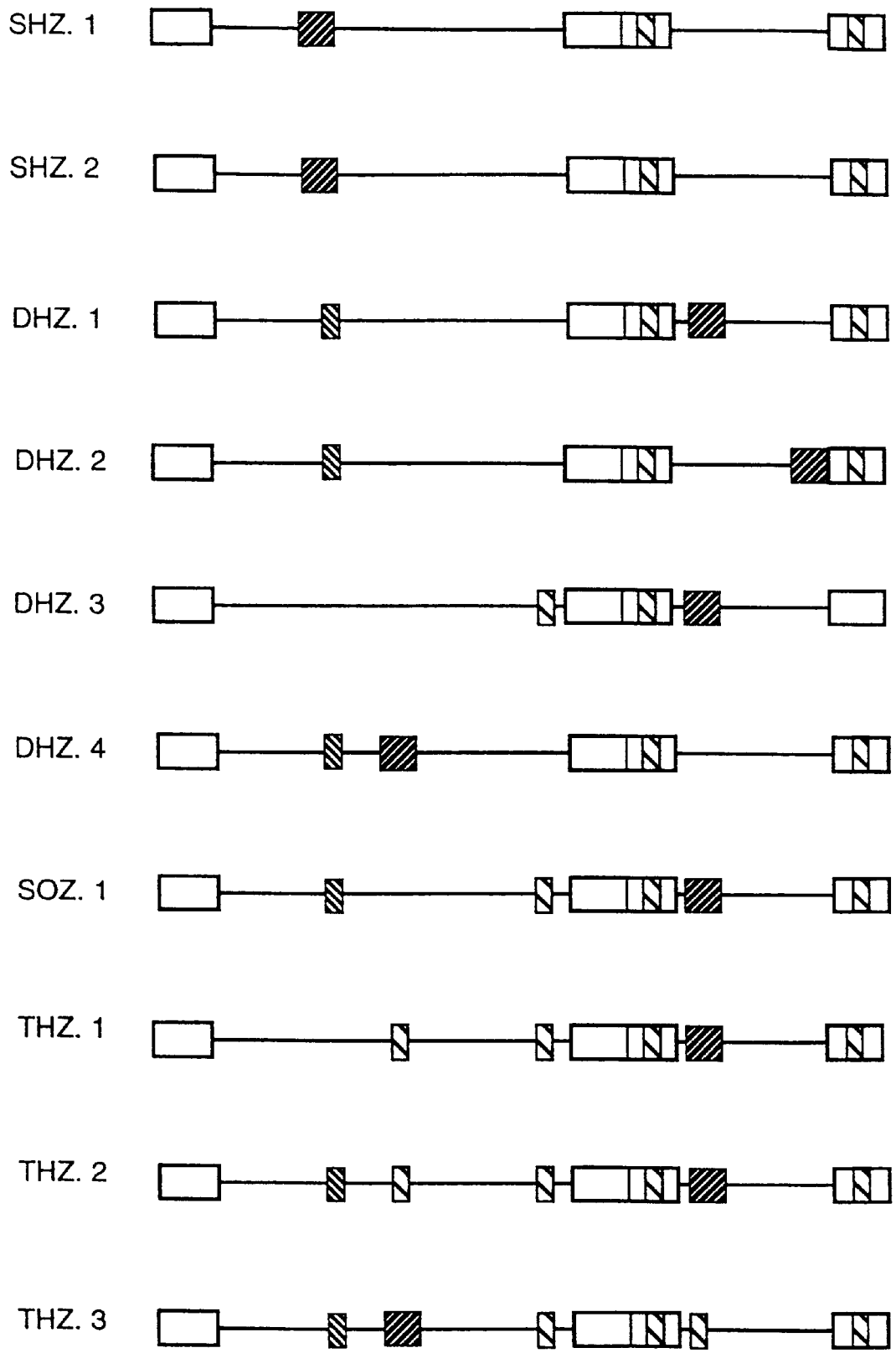
FIGS. 9A–9B are schematic representations of multideficient vectors created in accordance with the present inventive method.

This vector is tk$^-$, ICP4$^-$, and contains an HCMV-IEp-LacZ expression cassette at the native tk locus. SHZ.1 is represented in FIG. 9A. This vector was created to assay the ability to insert an exogenous polynucleotide at the lox cite in the Ktk-lox Vector.

SHZ.1 was created by cre-lox-mediated recombination between the d120 tk-lox HSV vector and the plox-II plasmid. Following the recombination reaction, the viruses were precipitated into E5 cells and assayed for blue plaques by the β-gal assay. Blue plaques were isolated and the correct insertion was confirmed by Southern blot hybridization.

Growth characteristics and genotype are presented in Table 1.

SHZ.2

This vector is ICP4$^-$ and contains both an HCMV-LacZ expression cassette and an HSV-ICP4-IEp-tk expression cassette at the tk locus. SHZ.1 is represented in FIG. 9A.

SHZ.2 was created by cre-lox-mediated recombination between the d120 tk-lox HSV vector and the plox-I plasmid. Following the recombination reaction, the viruses were The recombinant, termed ICP4TK KOS was crossed with the d120 vector via homologous recombination to produce a vector deficient for ICP4 and which had the HSV ICP4-IEp-tk cassette. Recombinants were screened for viruses that could form semi-syncytial plaques on E5 cells but not on VERO cells. One virus (S4TK, FIG. 10A, step A) was purified, and the genotype confirmed by Southern hybridization.

Growth characteristics and genotype are presented in Table 1.

SOZ.1

This vector is ICP4$^-$, and UL41$^-$ and contains an HSV-ICP4-IEp-tk expression cassette at the UL24 locus, and an HSV-ICP0-IEp-LacZ mutating cassette the UL41 locus. SOZ.1 is depicted in FIG. 9A and FIG. 10C, step F.

This vector was created by homologous recombination to insert the ICP0-IEp-LacZ mutating cassette from the pZ2 plasmid into the HSV UL41 locus of S4TK. Recombinants were screened by X-gal staining, and viral DNA from blue plaques was purified and subjected to Southern blot-analysis to confirm the correct insertion.

Growth characteristics and genotype are presented in Table 1.

DHZ.1

This vector is ICP4⁻ and ICP22⁻, and it contains an HSV-ICP4-IEp-tk expression cassette at the UL24 locus and an HCMV-IEp-lacZ-pA mutating cassette at the ICP22 locus. DHZ.1 is depicted in FIG. 9A.

To create the DHZ.1 vector, a KpnI-Not-I fragment from PB5 comprising the ICP22 homologous regions and the HCMV-IEp-lacZ-pA mutating cassette was co-transfected into E5 cells with the S4TK vector. Recombinants were screened for LacZ expression, and the correct insertion was confirmed with Southern blot analysis.

Growth characteristics and genotype are presented in Table 1.

Figure 9B:
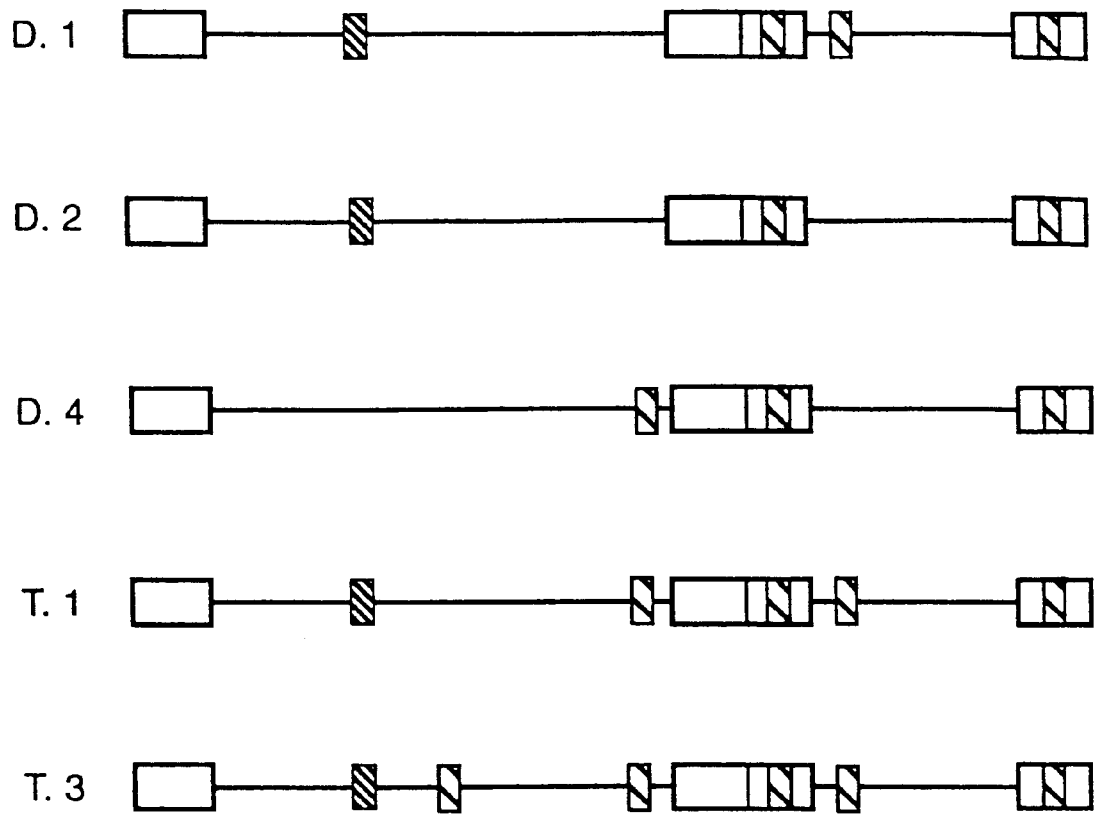

Subsequently, the D.1 vector was created by PacI excision. DHZ.1 DNA was digested with PacI to excise the lacZ expression cassette from the ICP22 locus. Viral DNA fragments were then transfected, and the resultant plaques were assayed for β-galactosidase activity. LacZ negative (i.e., white) plaques were selected and assayed for correct ligation by Southern analysis. A plaque with the correct excision (D.1, FIG. 9B) was amplified. D.1, thus, is ICP4⁻ and ICP22⁻ (by virtue of the excision of the PacI-flanked cassette), and it contains an ICP4-IEp-tk expression cassette at the UL24 locus but lacks LacZ.

DHZ.2

This vector is ICP4⁻ and ICP47⁻, and it contains an HSV-ICP4-IEp-tk expression cassette at the UL24 locus. DHZ.2 is depicted in FIG. 9A.

To create the DHZ.2 vector, a BglII-PmeI fragment from pko6 comprising the ICP47 homologous regions flanking the HCMV-IEp-pA cassette was co-transfected into E5 cells with the S4TK vector (FIG. 10A, Step B). Recombinants were screened for LacZ expression, and the correct insertion was confirmed with Southern blot analysis.

Growth characteristics and genotype are presented in Table 1.

Subsequently, the D.2 vector was created by PacI excision. DHZ.2 DNA was digested with PacI to excise the lacZ expression cassette from the ICP47 locus. Viral DNA fragments were then transfected, and the resultant plaques were assayed for β-galactosidase activity. LacZ negative (i.e., white) plaques were selected and assayed for correct ligation by Southern blot analysis. A plaque with the correct excision (D.2, FIG. 9B) was amplified. D.1, thus, is ICP4⁻ and ICP47⁻ (by virtue of the excision of the PacI-flanked cassette), and it contains an ICP4-IEp-tk expression cassette at the UL24 locus but lacks LacZ.

DHZ.3

This vector is tk⁺, ICP22⁻, and ICP27⁻ and contains the HCMV-IEp-lacZ-pA mutating cassette at the ICP22 locus. DHZ.3 is depicted in FIG. 9A.

To create the DHZ.3 vector, a KpnI-Not-I fragment from PB5 comprising the ICP22 homologous regions and the HCMV-LacZ-IEp-pA mutating cassette was co-transfected into N23 cells with the 5dl1.2 vector. Recombinants were screened for LacZ expression, and the correct insertion was confirmed with Southern blot analysis.

Growth characteristics and genotype are presented in Table 1.

THZ.1

This vector is ICP4⁻, ICP22⁻, and ICP27⁻, and it contains an ICP4-IEp-tk expression cassette at the UL24 locus and an HCMV-IEp-lacZ-pA mutating cassette at the ICP22 locus. THZ.1 is depicted in FIG. 9A.

This vector was created by homologous recombination between the DHZ.1 vector and the 5dl1.2 vector in 7B cells. Recombinants were screened by X-gal staining, and viral DNA from blue plaques was purified and subjected to Southern blot analysis to confirm the correct genotype.

Growth characteristics and genotype are presented in Table 1.

Subsequently, the T.1 vector was created by PacI excision. THZ.1 DNA was digested with PacI to excise the lacZ expression cassette from the ICP22 locus. Viral DNA fragments were then transfected, and the resultant plaques were assayed for β-galactosidase activity. LacZ negative (i.e., white) plaques were selected and assayed for correct ligation by Southern blot analysis. A plaque with the correct excision (T.1, FIG. 9B) was amplified. T.1, thus, is ICP4⁻, ICP22⁻, and ICP27⁻ (by virtue of the excision of the PacI-flanked cassette), and it contains an ICP4-IEp-tk expression cassette at the UL24 locus but lacks LacZ.

THZ.3

This vector is ICP4⁻, ICP22⁻, ICP27⁻, and UL41⁻, and it contains an ICP4-IEp-tk expression cassette at the UL24 locus and the HCMV-IEp-lacZ-pA mutating cassette at the ICP22 locus. THZ.3 is depicted in FIG. 9A.

This vector was created by homologous recombination between the THZ.1 vector and the ΔSma-UL41 vector in 7B cells. Recombinants were screened by X-gal staining, and viral DNA from blue plaques was purified and subjected to Southern blot analysis to confirm the correct genotype.

Growth characteristics and genotype are presented in Table 1.

Subsequently, the T.3 vector was created by PacI excision. THZ.3 DNA was digested with PacI to excise the lacZ expression cassette from the ICP22 locus. Viral DNA fragments were then transfected, and the resultant plaques were assayed for β-galactosidase activity. LacZ negative (i.e., white) plaques were selected and assayed for correct ligation by Southern analysis. A plaque with the correct excision (T.3, FIG. 9B) was amplified. T.3, thus, is ICP4⁻, ICP22⁻ (by virtue of the excision of the PacI-flanked cassette), ICP27⁻, and UL41⁻, and it contains an ICP4-IEp-tk expression cassette at the UL24 locus but lacks LacZ.

TOZ.1

This vector is ICP4⁻, ICP22⁻, ICP27⁻, and UL41⁻, and it contains an ICP4-IEp-tk expression cassette at the UL24 locus.

T.1 DNA and SOZ.1 DNA were co-transfected into 7B cells to promote homologous recombination. Resultant plaques were assayed for β-galactosidase activity and blue plaques further assayed for the ability to grow on E5 or N23 cells. The correct recombination was confirmed with Southern Analysis.

Growth characteristics and genotype are presented in Table 1.

Discussion

This example has demonstrated that novel HSV strains deficient for a multiplicity of native loci can readily be created using the insertion of a mutating cassette such as those described herein. Furthermore, this example evinces the power of the present inventive method at creating novel mutations in discrete loci by excising the double PacI cassette.

EXAMPLE 3 CREATION OF INSERTION MUTANTS

To investigate the efficiency of mutagenesis by the PAC1 recombination method, a variety of insertion mutants were constructed. Details concerning the creation of each vector are presented in the following subsections.

Efficiency was tested by noting the percentage of white plaques in the blue background (indicating any recombinant event) and by noting the percentage of correct insertions among white plaques (indicating the efficiency of correct insertion). The results are presented in Table 2.

TABLE 2

| Vector | Source | Insert | % White | Recombination |
|---|---|---|---|---|
| 3A3 | DHZ.1 | HCMV-hB7 in ICP22 | 88% | 20% |
| HvIL-10 | THZ.1 | SCMV-vIL-10 in ICP22 | 88% | 58% |
| HG1 | SOZ.1 | ICP0-hGM-CSF in UL41 | 100% | 58% |
| T/Hbcl2 | THZ.1 | HCMV-bcl-2 in ICP22 | 100% | 50% |
| DHIL2.2/ 167.1 | DHZ.2 | HCMV-hIL-2 in ICP47 | 100% | 65% |
| 6.8.1 | THZ.3 | HCMV-hB7.1 in ICP47 | 60% | 66% |
| PM15 | THZ.3 | HCMV-mB7.1 in ICP22 | 100% | 30% |
| MG2 | SOZ.1 | ICP0-mGM-CSE in UL41 | 80% | 19% |
| M7 | THZ.1 | HCMV-mucl in ICP22 | 100% | 15% |

3A3

This vector is ICP4$^-$ and ICP22$^-$, contains an HSV-ICP4-IEp-tk expression cassette at the UL24 locus, and contains an HCMV-IEp-hB7 expression cassette at the ICP22 locus.

DHZ.1 vector DNA was digested with Pac1, and the viral DNA was purified. A linear polynucleotide comprising an HCMV-IEp-hB7 expression cassette flanked by regions homologous to ICP22 was co-transfected with the viral DNA arms into 7B cells to promote recombination. The resultant plaques were assayed for β-galactosidase activity. LacZ negative (i.e., white) plaques were selected and assayed for correct recombination of the HCMV-IEp-hB7 expression cassette into the ICP22 locus by Southern blot analysis. The efficiency of this recombination is presented in Table 2.

HvIL-10

This vector is ICP4$^-$, ICP22$^-$, and ICP27$^-$; it contains an ICP4-IEp-tk expression cassette at the UL24 locus and an HCMV-IEp-vIL10 expression cassette at the ICP22 locus.

THZ.1 vector DNA was digested with Pac1, and the viral DNA was purified. A linear polynucleotide comprising an HCMV-IEp-vIL10 expression cassette flanked by regions homologous to ICP22 was co-transfected with the viral DNA arms into 7B cells to promote recombination. The resultant plaques were assayed for β-galactosidase activity. LacZ negative (i.e., white) plaques were selected and assayed for correct recombination of the HCMV-IEp-vIL10 expression cassette into the ICP22 locus by Southern analysis. The efficiency of this recombination is presented in Table 2.

HG1

This vector is ICP4$^-$ and UL41$^-$, and it contains an ICP4-IEp-tk expression cassette at the UL24 locus and an HSV-ICP0-hGM-CSF expression cassette at the UL41 locus (FIG. 10C, step F).

SOZ.1 vector DNA was digested with Pac1, and the viral DNA was purified. A linear polynucleotide comprising an HSV-ICP0-hGM-CSF expression cassette flanked by regions homologous to UL41 was co-transfected with the viral DNA arms into 7B cells to promote recombination. The resultant plaques were assayed for β-galactosidase activity. LacZ negative (i.e., white) plaques were selected and assayed for correct recombination of the HSV-ICP0-hGM-CSF expression cassette into the UL41 locus by Southern blot analysis. The efficiency of this recombination is presented in Table 2.

T/Hbcl2

This vector is ICP4$^-$, ICP22$^-$, and ICP27$^-$; it contains an ICP4-IEp-tk expression cassette at the UL24 locus and an HCMV-IEp-bcl2 expression cassette at the ICP22 locus.

THZ.1 vector DNA was digested with Pac1, and the viral DNA was purified. A linear polynucleotide comprising an HCMV-IEp-bcl2 expression cassette flanked by regions homologous to ICP22 was co-transfected with the viral DNA arms into 7B cells to promote recombination. The resultant plaques were assayed for β-galactosidase activity. LacZ negative (i.e., white) plaques were selected and assayed for correct recombination of the HCMV-IEp-bcl2 expression cassette into the ICP22 locus by Southern blot analysis. The efficiency of this recombination is presented in Table 2.

DHIL2.2/167.1

This vector is ICP4$^-$ and ICP47$^-$, and it contains an HCMV-LacZ expression cassette at the UL24 locus and an HCMV-IL2 expression cassette at the ICP47 locus (FIG. 10, steps C–D).

DHZ.2 vector DNA was digested with Pac1, and the viral DNA was purified. A linear polynucleotide comprising an HCMV-IEp-bcl2 expression cassette flanked by regions homologous to ICP47 was co-transfected with the viral DNA arms into 7B cells to promote recombination. The resultant plaques were assayed for β-galactosidase activity. LacZ negative (i.e., white) plaques were selected and assayed for correct recombination of the HCMV-IEp-bcl2 expression cassette into the ICP47 locus by Southern blot analysis. The efficiency of this recombination is presented in Table 2.

6.8.1

This vector is ICP4$^-$, ICP22$^-$, ICP27$^-$, and UL41$^-$; it contains an ICP4-IEp-tk expression cassette at the UL24 locus and an HCMV-IEp-hB7.1 expression cassette at the ICP22 locus.

THZ.3 vector DNA was digested with Pac1, and the viral DNA was purified. A linear polynucleotide comprising an HCMV-IEp-hB7.1 expression cassette flanked by regions homologous to ICP22 was co-transfected with the viral DNA arms into 7B cells to promote recombination. The resultant plaques were assayed for β-galactosidase activity. LacZ negative (i.e., white) plaques were selected and assayed for correct recombination of the HCMV-IEp-hB7.1 expression cassette into the ICP22 locus by Southern blot analysis. The efficiency of this recombination is presented in Table 2.

PM15

This vector is ICP4$^-$, ICP22$^-$, ICP27$^-$, and UL41$^-$; it contains an ICP4-IEp-tk expression cassette at the UL24 locus and an HCMV-IEp-mB7.1 expression cassette at the ICP22 locus.

THZ.3 vector DNA was digested with Pac1, and the viral DNA was purified. A linear polynucleotide comprising an HCMV-IEp-mB7.1 expression cassette flanked by regions homologous to ICP22 was co-transfected with the viral DNA arms into 7B cells to promote recombination. The resultant plaques were assayed for β-galactosidase activity. LacZ negative (i.e., white) plaques were selected and assayed for correct recombination of the HCMV-IEp-mB7.1 expression cassette into the ICP22 locus by Southern blot analysis. The efficiency of this recombination is presented in Table 2.

MG2

This vector is ICP4$^-$ and UL41$^-$, and it contains an ICP4-IEp-tk expression cassette at the UL24 locus and an HSV-ICP0-mGM-CSF expression cassette at the UL41 locus.

SOZ.1 vector DNA was digested with Pac1, and the viral DNA was purified. A linear polynucleotide comprising an HSV-ICP0-mGM-CSF expression cassette flanked by regions homologous to UL41 was co-transfected with the viral DNA arms into 7B cells to promote recombination. The resultant plaques were assayed for β-galactosidase activity. LacZ negative (i.e., white) plaques were selected and assayed for correct recombination of the HSV-ICP0-mGM-CSF expression cassette into the UL41 locus by Southern blot analysis. The efficiency of this recombination is presented in Table 2.

M7

This vector is ICP4⁻, ICP22⁻, ICP27⁻, and UL41⁻; it contains an ICP4-IEp-tk expression cassette at the UL24 locus and an HCMV-IEp-muc1 expression cassette at the ICP22 locus.

THZ.3 vector DNA was digested with Pac1, and the viral DNA was purified. A linear polynucleotide comprising an HCMV-IEp-muc1-pA expression cassette not flanked by regions homologous to ICP22 (but flanked by regions homologous to the HCMV and pA sequences of the insertion cassette) was co-transfected with the viral DNA arms into 7B cells to promote recombination. The resultant plaques were assayed for β-galactosidase activity. LacZ negative (i.e., white) plaques were selected and assayed for correct recombination of the HCMV-IEp- muc1 expression cassette into the ICP22 locus by Southern blot analysis. The efficiency of this recombination is presented in Table 2.

Discussion

This example details the creation of nine separate insertion mutants via the present inventive method. Moreover, the data presented in Table 2 indicate that the present inventive method for introducing a foreign expression cassette into a targeted position within the HSV genome results in the correct insertion approximately 38% of the time. Lastly, the data indicate that viral flanking regions are not necessary to produce desired recombinants. Thus, the Pac1 recombination method for creating mutant HSV viruses is significantly more efficient than traditional methods for creating predefined HSV deletions/insertions.

EXAMPLE 4 CREATION OF MULTIGENE HSV VECTORS

To examine the feasibility of performing successive rounds of Pac1 mutagenesis, a series of successive rounds was conducted, in combination with homologous recombination, to develop an HSV vector in which 4 exogenous expression cassettes operate in a background lacking four native HSV loci. This mutagenesis scheme is graphically represented in FIGS. 10A–10C.

7G6

Figure 10B:
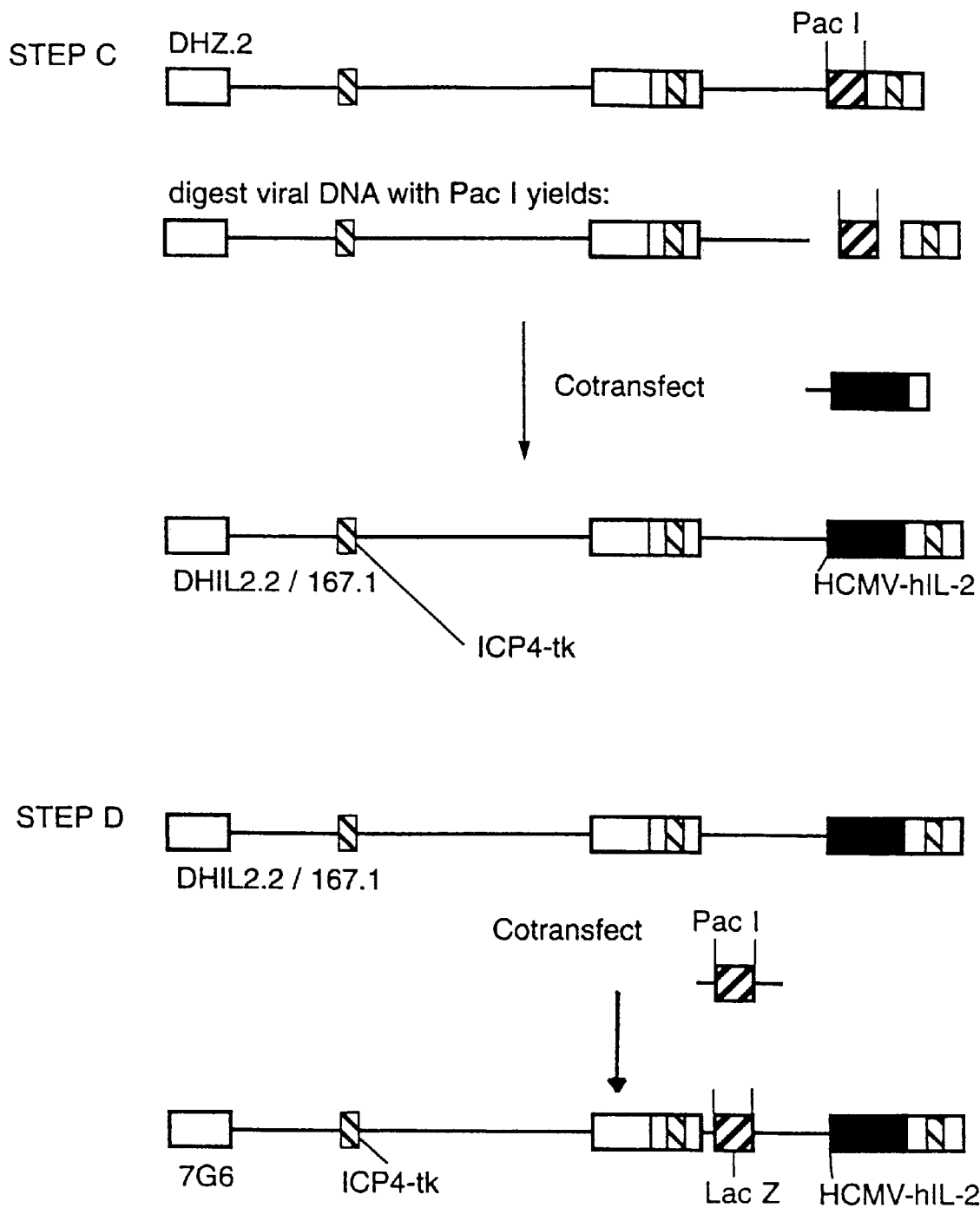
Figure 10C:
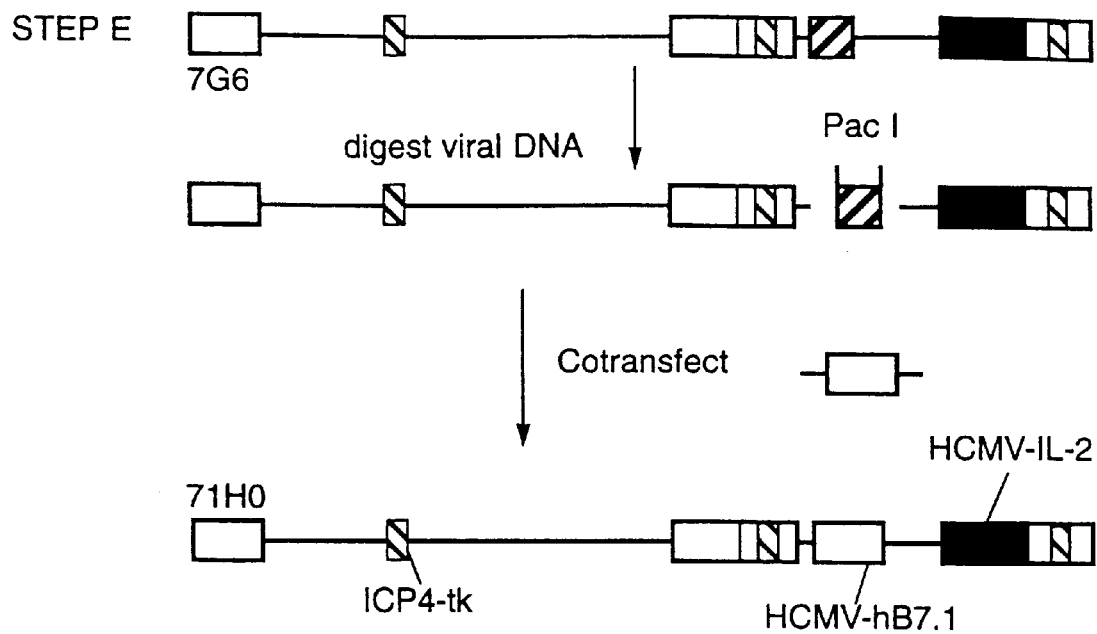
Figure 10C:
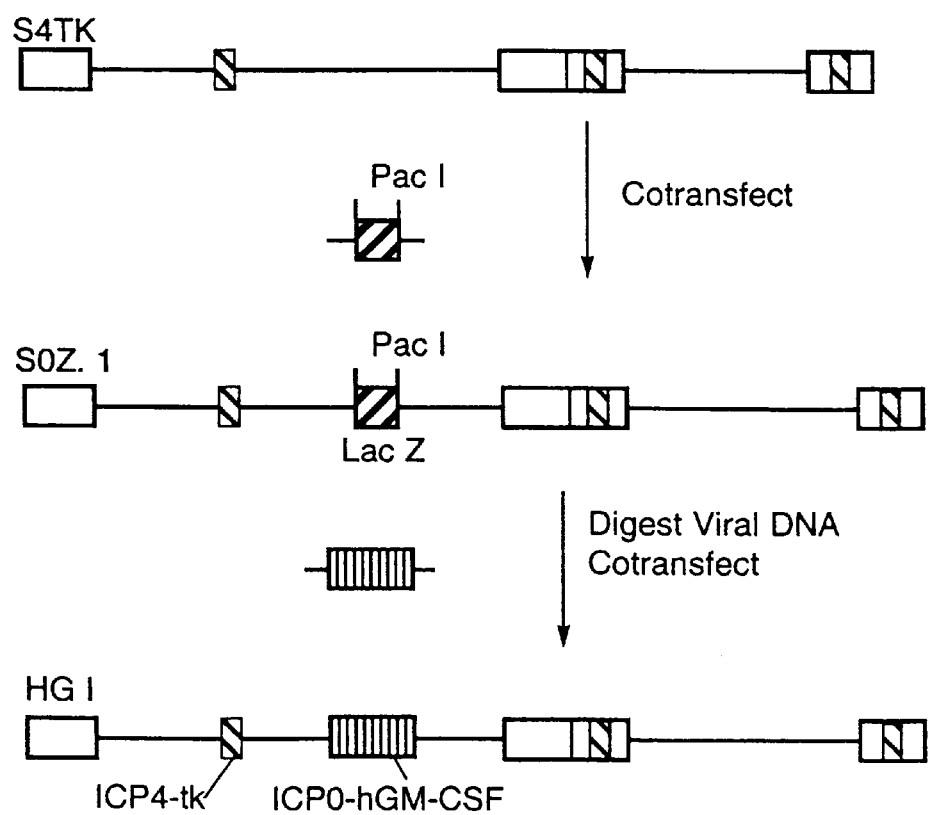

This vector is ICP4⁻, ICP22⁻, and ICP47⁻, and it contains an ICP4-IEp-tk expression cassette at the UL24 locus and an HCMV-IL2 expression cassette at the ICP47 locus (FIG. 10B, step D).

To create the 7G6 vector, a KpnI-Not-I fragment from PB5 comprising the ICP22 homologous regions and the HCMV-IEp-LacZ-pA cassette from pRC2 was co-transfected into 7B cells with the DHIL2.2/167.1 vector (FIG. 10B, step D). Recombinants were screened for LacZ expression, and the correct insertion was confirmed with Southern blot analysis.

7H10

This vector is ICP4⁻, ICP22⁻, and ICP47⁻, and it contains an ICP4-IEp-tk expression cassette at the UL24 locus, an HCMV-IL2 expression cassette at the ICP47 locus, and an HCMV-IEp-hB7.1 expression cassette at the ICP22 locus (FIG. 10B, step E).

To create the 7H10 vector, 7G6 vector DNA was digested with Pac1, and the viral DNA was purified. A linear polynucleotide comprising an HCMV-IEp-hB7.1 expression cassette flanked by regions homologous to ICP22 was co-transfected with the viral DNA arms into 7B cells to promote recombination (FIG. 10B, step E). The resultant plaques were assayed for β-galactosidase activity. LacZ negative (i.e., white) plaques were selected and assayed for correct recombination of the HCMV-IEp-hB7.1 expression cassette into the ICP22 locus by Southern blot analysis.

HGZ.25

Figure 10D:
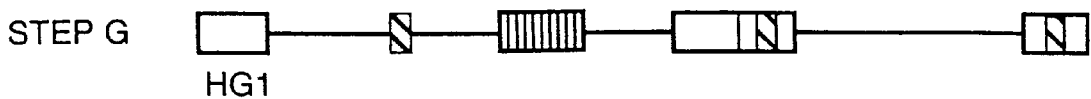
Figure 10D:
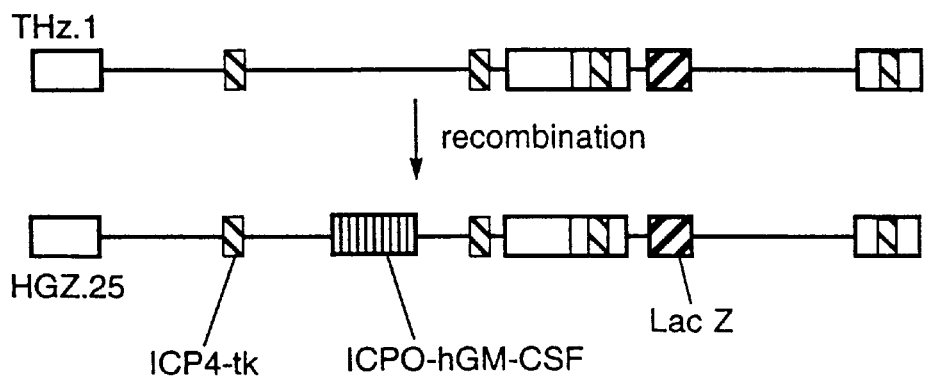
Figure 10D:
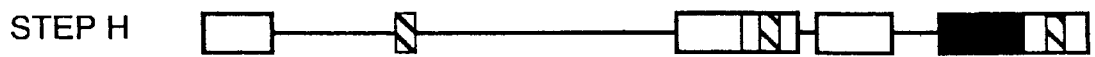
Figure 10D:
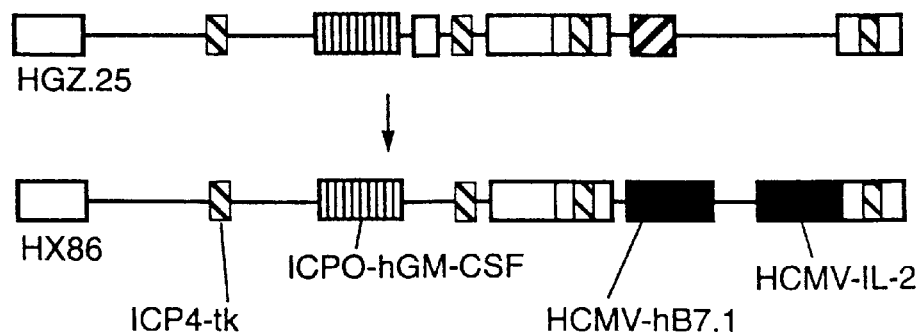

This vector is ICP4⁻, ICP27⁻, ICP22⁻, and UL41⁻, and it contains an HSV-ICP4-IEp-tk expression cassette at the UL24 locus, an HSV-ICP0-hGM-CSF expression cassette at the UL41 locus, and an HCMV-IEp-lacZ-pA mutating cassette at the ICP22 locus (FIG. 10D, Step G).

HG.1 and THZ.1 were co-infected into 7B cells to promote homologous recombination. Resultant plaques were assayed for β-galactosidase activity and blue plaques further assayed for the inability to grow on E5 or N23 cells. The correct recombination was confirmed with Southern blot analysis.

HX86

This vector is ICP4⁻, ICP27⁻, ICP22⁻, ICP47⁻, and UL41⁻; it contains an HSV-ICP4-IEp-tk expression cassette at the UL24 locus, an HSV-ICP0-hGM-CSF expression cassette at the UL41 locus, a HCMV-IEp-hB7.1 expression cassette at the ICP22 locus, and a HCMV-IEp-hIL2 expression cassette at the ICP47 locus (FIG. 10D, step H).

7H10 and HGZ.25 were co-infected into 7B cells to promote homologous recombination to result in a crossover event between the UL41 locus and the ICP22 locus. Resultant plaques were assayed for β-galactosidase activity, and white plaques were further assayed for the inability to grow on E5 or N23 cells. The correct recombination was confirmed with Southern blot analysis.

HX86Z

This vector is ICP4⁻, ICP27⁻, ICP22⁻, ICP47⁻, gC⁻ and UL41⁻; it contains an HSV-ICP4-IEp-tk expression cassette at the UL24 locus, an HSV-ICP0-Iep-hGM-CSF expression cassette at the UL41 locus, an HCMV-IEp-hB7.1 expression cassette at the ICP22 locus, a HCMV-IEp-hIL2 expression cassette at the ICP47 locus, and an HCMV-IEp-LacZ Pac1 mutating cassette at the gC locus.

To create the HX86Z vector, a polynucleotide comprising a gC ICP22 homologous regions and the HCMV-LacZ-IEp-pA mutating cassette were co-transfected into N23 cells with the HX86 vector. Recombinants were screened for LacZ expression, and the correct insertion was confirmed with Southern blot analysis.

Expression

Expression of each of the transgenes from the multigene HSV vector HX86 was observed.

Expression of the HCMV-IEp-hB7.1 expression cassette at the ICP22 locus was assayed via FACS analysis 24 hours post infection. Depending on MOI, about 50–70% of HX86-infected cells tested positive for hB7.1 expression, compared to about 5–10% for control cells.

Expression of the HSV-ICP0-Iep-hGM-CSF expression cassette at the UL41 locus was assayed via ELISA analysis 48 hours post infection. Independent of MOI (MOI of 1 and 3 tested), between about HX86-infected cells expressed approximately 210 ng/$10^6$ cells, compared to less than 50 ng/$10^6$ cells for all controls.

Expression of the HCMV-IEp-hIL2 expression cassette at the ICP47 locus was assayed via ELISA analysis 48 hours post infection. At MOIs of 1 and 5, cells infected with HX86 produced 100 and 140 pg hIL2/$10^6$ cells, respectively, compared to controls which exhibited virtually no hIL2 production.

Expression of the HSV-ICP4-IEp-tk expression cassette at the UL24 locus was assayed via gancyclovir selection analysis three days post infection. Uninfected Vero or MCA207 cells exhibited vigorous growth (cell count in millions of cells) both in the presence and absence of 10 μg/ml gancyclovir. Cells infected with HX86, however, exhibited vigorous growth only in the absence of gancyclovir. Upon treatment with 10 μg/ml gancyclovir, no infected cells, or only a very few infected cells, were present.

Discussion

This example demonstrates that the present inventive method can create multigene vectors in which multiple non-native HSV expression cassettes are introduced into a single HSV vector. These results also demonstrate a multigene HSV vector of the present invention comprising four separate expression cassettes, each cassette located in a discrete genetic locus, each cassette expressing a coding polynucleotide in biologically active form, and each cassette expressing its coding polynucleotide under independent and kinetically distinguishable regulatory control.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments can be used and that it is intended that the invention can be practiced otherwise than as specifically described herein. Accordingly, this invention includes all modifications encompassed within the spirit and scope of the invention as defined by the following claims.

What is claimed is:

1. A method of preparing a Herpes Simplex Virus (HSV) vector which comprises:

a) co-transfecting a source HSV vector and a mutating cassette together into a population of host cells;

wherein said mutating cassette comprises polynucleotides homologous to a region of the HSV genome and flanking a restriction site not present in the sequence of said source vector;

b) plaquing the population of co-transfected host cells;

c) selecting plaques comprising cells in which recombination has occurred between said source vector and said mutating cassette;

d) isolating the viral DNA from said plaques;

e) digesting the isolated viral DNA with a single restriction endonuclease appropriate for cleaving said viral DNA at said restriction site within said mutating cassette, whereby two viral polynucleotides derived from said source HSV vector are produced;

f) isolating and purifying said two viral polynucleotides; and g) joining said two viral polynucleotides derived from said source HSV vector and an insertion cassette to form an HSV vector comprising the insertion cassette at the former locus of the restriction site, wherein said restriction site is not reconstructed.

2. The method of claim 1, wherein said restriction site is Pac1.

3. The method of claim 1, wherein said mutating cassette comprises two restriction sites not present in the sequence of said source HSV vector.

4. The method of claim 3, wherein said two restriction sites are identical restriction sites which flank a region for excision.

5. The method of claim 1, wherein said mutating cassette is an expression cassette.

6. The method of claim 5, wherein said mutating cassette encodes a selectable marker, whereby said recombinant viral DNA is isolated from plaques in which said selectable marker is expressed.

7. The method of claim 6, in which said selectable marker is β-galactosidase.

8. The method of claim 1, wherein said source vector is deficient in an HSV native locus.

9. The method of claim 8, wherein said source vector is replication incompetent.

10. The method of claim 1, wherein said insertion cassette is an expression cassette.

11. The method of claim 10, wherein said insertion cassette encodes RNA.

* * * * *